United States Patent [19]

Logemann et al.

[11] Patent Number: 5,428,146
[45] Date of Patent: Jun. 27, 1995

[54] WOUND-STIMULATED DNA-SEQUENCE FROM SOLANUM TUBEROSUM AND ITS USE

[75] Inventors: Jürgen Logemann, Erftstadt; Lothar Willmitzer, Berlin; Josef Schell, Köln, all of Germany

[73] Assignee: Max-Planck-Gesellschaft zur Forderung, Germany

[21] Appl. No.: 50,770

[22] Filed: Apr. 21, 1993

Related U.S. Application Data

[63] Continuation of Ser. No. 690,946, May 2, 1991, abandoned.

[30] Foreign Application Priority Data

Nov. 7, 1988 [DE] Germany ............... 38 37 752.7

[51] Int. Cl.$^6$ ............ C07H 21/04; C12N 15/00; A01H 1/04
[52] U.S. Cl. .................. 536/24.1; 435/320.1; 800/205; 800/DIG. 42; 800/DIG. 43; 536/23.6
[58] Field of Search ............ 435/320.1, 172.3; 800/205, DIG. 42, DIG. 43; 536/23.1, 24.1, 23.6; 935/6, 9, 35, 67

[56] References Cited

FOREIGN PATENT DOCUMENTS 8700865 2/1987 WIPO .

OTHER PUBLICATIONS

Logemann et al., "Improved Method for the Isolation of RNA from Plant Tissues", Anal. Bioch. 163:16–20 (1987).
Sanchez-Serano et al., "Nucleotide Sequence of Proteinase Inhibitor II Encoding cDNA of Potato (*Solanum tuberosum*) and its Mode of Expression", Mol. Gen. Genet., 203:15–20 (1986).
Joshi, "An Inspection of the Domain Between Putative TATA box and Translation Start Site in 79 Plant Genes", Nuc. Acids Res., 15:6643–6653 (1987).
Benoist et al., "The Ovalbumin Gene-Sequence of Putative Control Regions", Nuc. Acids Res., 8:127–142 (1980).
Zambryski et al., "Ti Plasmid Vector for the Introduction of DNA into Plant Cells Without Alteration of Their Normal Regeneration Capacity", EMBO J., 2:2143–2150 (1983).
Jefferson et al., "–Glucuronidase from *Escherichia coli* as a Gene-Fusion Marker", Proc. Natl'l. Acad. Sci. U.S.A., 83:8447–8451 (1986).
Velten et al., "Selection-Expression Plasmid Vectors for use in Genetic Transformation of Higher Plants", Nucl. Acids Res., 13: 6981–6998 (1985).
Langride et al., "Dual Promoter of *Agrobacterium tumefaciens* Mannopine Synthase Genes Is Regulated By Plant Growth Hormones", Proc. Natl. Acad. Sci. USA, 86:3219–3223 (1989).
Teeri et al., "Gene Fusions To LacZ Reveal New Expression Patterns of Chimeric Genes in Transgenic Plants", EMBOJ., 8:343–350 (1989).
Maniatis et al., "Molecular Cloning: A Laboratory Manual", Cold Spring Harbour Laboratory, Cold Spring Harbor, New York (1982) pp. 61–73.
Murashige et al., "A Revised Medium for Rapid Growth and Bio Assays with Tobacco Tissue Cultures", Physiol. Plan. 15:473–477 (1962).

(List continued on next page.)

*Primary Examiner*—David T. Fox
*Assistant Examiner*—Charles C. P. Rories
*Attorney, Agent, or Firm*—Brumbaugh, Graves, Donohue & Raymond

[57] ABSTRACT

The invention relates to wound-stimulated DNA from *Solanum tuberosum* as well as parts thereof, their use for the development of gene products in higher plants using wounding or pathogen attack, DNA-transfer vectors containing these, and plants or plant portions containing these. The promoter of this DNA-sequence can be used for the expression of gene products in higher plants using wound and/or pathogen attack.

7 Claims, 15 Drawing Sheets

OTHER PUBLICATIONS

Messing et al., "Filamentous Coliphage M13 as a Cloning Vehicle: Insertion of a HindII Fragment of the lac Regulatory Region in M13 replicative form In Vitro", Proc. Natl. Acad. Sci., 74: 3642–3646 (1977).

Van Haute et al, "Intergeneric Transfer and Exchange Recombination of Restriction Fragments Cloned in pBR322: A Novel Strategy for the Reversed Genetics of the Ti Plasmids of *Agrobacterium tumefaciens*", EMBO J., 2:411–417 (1983).

Vieira and Messing, "The pUC Plasmids, an M13mp7–derived system for Insertion Mutagenesis and Sequencing with Synthetic Universal Primers", Gene, 19:259–268 (1982).

Eckes et al., "Isolation and Characterization of a Light-Inducible, Organ-Specific Gene From Potato and Analysis of its Expression After Tagging and Transfer into Tobacco and Potato Shoots", Mol. Gen. Genet., 205:14–22 (1986).

Prols et al., "Transient Gene Expression in Tobacco Protoplasts: I. Time Course of CAT Appearance", Plant Cell Reports, 7:221–224 (1988).

Hain et al., "Uptake, Integration, Expression and Genetic Transmission of a Selectable Chimaeric Gene by Plant Protoplasts", Mol. Gen. Genet., 199:166–168 (1985).

Frischauf et al., "Lambda Replacement Vectors Carrying Polylinker Sequences", J. Mol. Biol., 170:827–842 (1983).

Yanisch-Perron et al., "Improved M13 Phase Cloning Vectors and Host Strains: Nucleotide Sequences of the M13mp18 and pUC19 Vectors", Gene, 33:103–119 (1985).

Werner et al., "Isolation of Poly(A) RNA by Paper Affinity Chromatography", Analytical Biochem., 141:329–336 (1984).

Lehrach et al., "RNA Molecular Weight Determination by Gel Electrophoresis under Denaturing Conditions, a Critical Reexamination", Biochemistry, 16:4743–4751 (1977).

Willmitzer et al., "The TL-DNA in Octopine Crown-Gall Tumours Code for Seven Well-Defined Polyadenylated Transcripts", EMBO J., 1:139–146 (1982).

Bedbrook, "A Plant Nuclear DNA Preparation Procedure", PMB Newsletter II, 24 (1981).

Wassenegger, "Einfuhrung und Expression Prokaryontischer DNA–Methyltransferasen in Nicotiana Tabacum", Dissertation, Koln (1988).

Southern, "Detection of Specific Sequences Among DNA Fragments Separated by Gel Electrophoresis", J. Mol. Biol., 98:503–517 (1975).

Lipphardt, "UV-Induzierbare Transiente Expression eines Chimaren Chalkonsynthase–NPTII–Gens in Petersilie-Protoplasten", Dissertation, Koln (1988).

Lorz et al., "Gene Transfer to Cereal Cells Mediated by Protoplast Transformation", Mol. Gen. Genet., 199:178–182 (1985).

Murray et al., "Rapid Isolation of High Molecular Weight Plant DNA", Nuc. Acid Res., 8:4321–4325 (1980).

Gorman et al., "Recombinant Genomes Which Express Chloramphenicol Acetyltransferase in Mammalian Cells", Mol. Cell. Biol., 2:1044–1051 (1982).

Reiss et al., "A New Sensitive Method for Qualitative and Quantitative Assay of Neomycin Phosphotransferase in Crude Cell Extracts", Gene, 30:211–218 (1984).

Schreier et al., "The Use of Nuclear-Encoded Sequences to Direct the Light-Regulated Synthesis and Transport of a Foreign Protein into Plant Chloroplasts", EMBO J., 4:25–32 (1985).

Herrera-Estrella et al., "Chimeric Genes As Dominant Selectable Markers in Plant Cells", EMBO J., 2:987–995 (1983).

Koncz et al., "The Promoter of TL-DNA Gene 5 Controls the Tissue-Specific Expression of Chimeric Genes Carried By A Novel Type of Agrobacterium Binary Vector", Mol. Gen. Genet. 204:383–396 (1986).

Koncz et al., "Expression and Assembly of Functional Bacterial Luciferase in Plants", Proc. Natl. Acad. Sci. USA, 84:131–135 (1987).

Topfer et al., "Versatile Cloning Vectors For Transient Gene Expression and Direct Gene Transfer in Plant Cells", Nucl. Acids Res., 16:8725.

Siebertz et al., "cis-Analysis of the Wound-Inducible Promoter Wun1 in Transgenic Tobacco Plants and Histochemical Localization of Its Expression", The Plant Cell, 1:961–968 (1989).

Jefferson et al., "GUS-Fusions: $\beta$-Glucuronidase As A Sensitive and Versatile Gene Fusion Marker in Higher Plants", EMBO J., 6: 3901–3907 (1987).

(List continued on next page.)

OTHER PUBLICATIONS

Logemann et al., "5′ Upstream Sequences From the wunl-Gene Are Responsible For Gene Activation By Wounding In Transgenic Plants", The Plant Cell, 1:151-158 (1989).

Dynan, W. S., "Modularity in Promoters and Enhancers", Cell, vol. 58 (1989) pp. 1-4.

Takahashi, K., et al. "Requirement of stereospecific alignments for initiation from the simian virus", Nature, vol. 319 (1986) pp. 121-126.

Payne, G., et al. "Isolation of the genomic clone for pathogenesis-related protein Ia from *Nicotiana tabacum* cv. Xanthi-nc", Plant Molecular Biology, vol. 11 (1988) pp. 89-94.

Müller et al., "Enhancer sequences and the regulation of gene transcription" Eur. J. Biochem., vol. 176 (1988) pp. 485-495.

Kay, R., et al. "Duplication of CaMV 35S Promoter Sequences Creates a Strong Enhancer for Plant Genes", Science, vol. 236 (1987) pp. 1299-1302.

R. Thornberg et al. P.N.A.S., vol. 84 (1987) pp. 744-748.

J. Logemann et al. P.N.A.S. vol. 85 (1988) pp. 1136-1140.

J. Sanchez≧Serrano et al. The EMBO Journal, vol. 6, No. 2 (1987) pp. 303-306.

```
  1 AAAGGGGTGGTGCTCGCCCTATATGAAGCCTTGAGCTCACACGACGTCGTTCAGGTCCAG

61 AAACTACTGGCCTCCGACCTCGAGTGGTGGTTCCATGGTCCTCCTTCTCATCAATTTTTG

121 ATGCAAATACTCACCGGCACTGCTAAATTCGATAACGCCTCTTTTCAATTCCTTCATAAG
     M  Q  I  L  T  G  T  A  K  F  D  N  A  S  F  Q  F  L  H  K

181 ACCATTGACGTATTCGGTTCCGTTGTTCTCGTTGAAGGTTGTGACCCAACCCGATCTATT
     T  I  D  V  F  G  S  V  V  L  V  E  G  C  D  P  T  R  S  I

241 ACTTGGGTTCACGCCTGGACTGTTACAGATGGGGTAATTACCCAGGTTAGGGAGTATTTC
     T  W  V  H  A  W  T  V  T  D  G  V  I  T  Q  V  R  E  Y  F

301 AATACCTCACTTACTGTCACCCGTTTTGGGAAATCGGATATTTCCTCAATTACGACTCTG
     N  T  S  L  T  V  T  R  F  G  K  S  D  I  S  S  I  T  T  L

361 CATTGCCCATCTGTTTGGGAGAGTAGCTTACCTAATCGGGTCGGAAAATCTGTTCCGGGT
     H  C  P  S  V  W  E  S  S  L  P  N  R  V  G  K  S  V  P  G

421 CTTGTATTGGCTCTATAAGAAACGACCCGATTTGTGCTGGCGTTGTATCTTGTGTCTAGT
     L  V  L  A  L  End

481 AGGATGTAAGATTAACGCGGCTGGTTTGGGATTCTGTTGCTATTTGGTTTGATTTGGTTT

541 GTTTTTATTTTTTAAGTTGGGATTTGTGTTCTGTTTATTATTTGTTGTTGTGATTGAGTT

601 AAAGAAGGGGCCAATGATAATTGGATATACCTTTCTACTCAATAGATTGTCTAATTATGT

661 ATTGGTTTGCAATAAAAGCATATTGATTGGCTGTTTAAAAAAAAAAAAAAA
```

FIG. 2

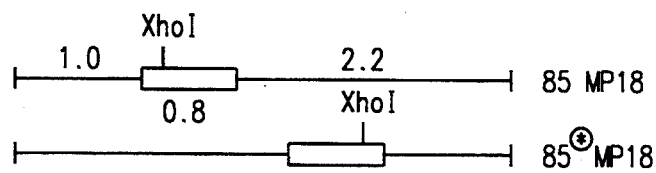
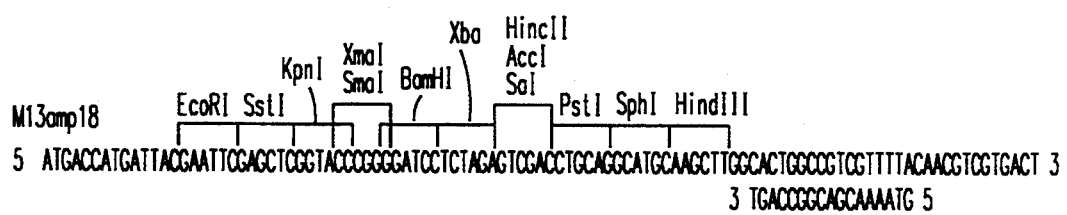
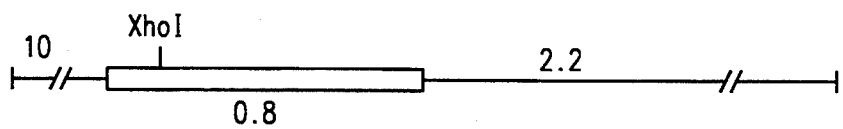
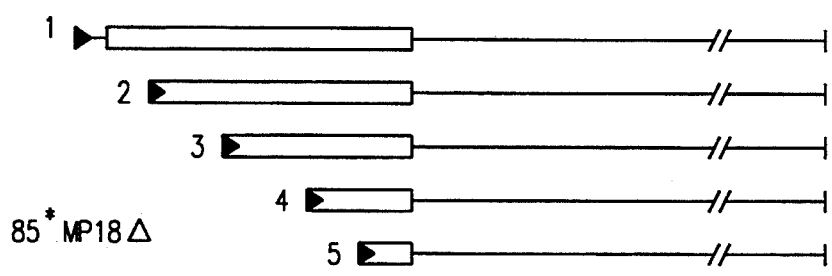
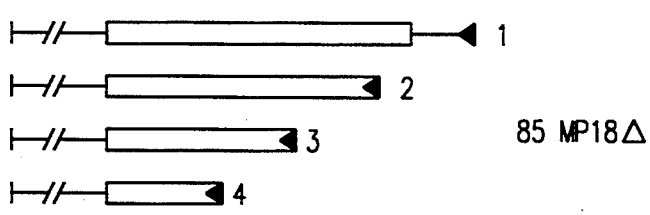
FIG. 5

5' 1        AAATTTTATACATACATACAAAGACAATCATTGATACATAACAA

45   TGATGTACATATATACAATTATCTAACCGATATATATATATATATATATATATATATA

105  TCACCTCTCTCCACTCTCTGCCCTCTCTTCATTCTCTCCCAATCTCGCTCACCACTCTAG

165  CCTAACATAGAGAACATATACATATACAAACACAATTTTCATAGACACAAATGGAATTAA

225  TACCTGATTTATATAAATCGCCGTGATTTATACAAATCAGATGCTCCATAACAAACATAA

285  TTTGACCCATGGAGTGCATATAACAAAATTGTAGCTATAGAACGCTAATATGTTTTTCTT

345  AATCTTTGTTATTCCTAAAATTTACTCATAATAATACTCTTTATAAAAGCATAAGCTGGT

405  TTGGTTTAGGGTTAGAGTATTCTCTAAAAATTCTAATTGAAATCAAATACATCTTATAGA

465  ATCCAAATTAGAATTGAACACGTCTTGTAGAGTCCCATAAATTTTTAATGTCTACAATGT

525  AATATCGTTAAAATATTTTAATATCTTGTTGAAATATAATTTTTTATTTAGTAAAATAAT

585  ATGAGAATTAATTTTTTTTATTAATCTTCACAACTATGATTTTTTTAAAATTTCATGTAA

645  ATATATGGGCTAAGATTGTGAGCCAACTGGTCAAAACTCAAAAGTTAGTCGAGTTTGAAT

705  GAAGTTAAAATTAAAAGTATTGTTGTCATAACTCATATGTTGCAAGTTGCAACTGTGTGT

765  ATAACGTCAAAAAAGGTATGCTTGAAAGTTGAAACTTTAGATATGACGATCATCTTCGTG

825  GGCCCTACCTAAAATAAAACGTCTCTTCATCATCCGAATATCACATCATCACGTAATCCC

885  CGAGCACGTGGAATGGCGCGTAAATATCATGTCGCCCTTTAAACCTAAATACACCTACTA

945  TTCACCTATAATTTCCAAACTACCCTTCCAACGTCCCTATATATTCCCCACATCACACCT

1005 CTTTCTTCATTACCTACCATACCTTCTTCTCTCATCCTTCATAGCTAATAATATCATCTT

1065 CTGTTTTTACTGAACTGGCTAACTCTCAGTTAACTCTGGAGGAAACAACAAACAAAGGGG

1125 TGGTGCTCGCCCTATATGAAGCCTTGAGCTCACACGACGTCGTTCAGGTCCAGAAACTCC

1185 TGGCCTCCGACCTCGAGTGGTGGTTCCATGGTCCTCCTTCTCATCAATTTTTGATGCAAA
                                                          M  Q  I

1245 TACTCACCGGCACTGCTAAATTCGATAACGCCTCTTTTCAATTCCTTCATAAGACCATTG

```
1305 ACGTATTCGGTTCCGTTGTTCTCGTCGAAGGCTGTGACCCGACCCGATCTATTACTTGGG
      V  F  G  S  V  V  L  V  E  G  C  D  P  T  R  S  I  T  W  V

1365 TTCACGCCTGGACTGTTACGGATGGGGTAATTACCCAGGTTAGGGAGTATTTCAATACCT
      H  A  W  T  V  T  D  G  V  I  T  Q  V  R  E  Y  F  N  T  S

1425 CACTTACTGTCACCCGTTTTGGGAAATCGGATATTTCCTCAATTACGACTCTGCATTGCC
      L  T  V  T  R  F  G  K  S  D  I  S  S  I  T  T  L  H  C  P

1485 CATCTGTTTGGGAGAGTAGCTTACCAAATCGGGTCGGAAAATCTGTTCCGGGTCTTGTAT
      S  V  W  E  S  S  L  P  N  R  V  G  K  S  V  P  G  L  V  L

1545 TGGCTCTATAAGAAACGACCCGATTTGTGGCTGGCGTTATATCTTGTGTCTAGTAGGATG
      A  L  END

1605 TAAGATTAACGCGGCTGGTTTGGGATTCTGTTGCTGCTGTTTGGTTTGTTTTTATTTTTT

1665 AAGTTGGGATTTGTGTTCTGTTTATTATTTGTTGTTGTGATTGAGTTAAAGAAGGGGCCA

1725 ATGATAATTGGATATACCTTTCTACTCAATAGATTGTCTAATTATGTGTTGGTTTGCAAT

1785 AAAAAGCATATTGATTGGCTGTTTACAAAATGTGTATATTTTTCAATTTGGTATTGCTTC

1845 TTGTTTTCAACGAATGACGATGGATACCGTGGAAACAATTTCATTGAAAGGCAAATCTTA

1905 TTATTAATGATGGAATCAGAATTTTTATTATGAGGTTTAAATAATTAAACATATAAAATA

1965 GTTAAATGAGGTTCGAAATCTATATAATGCATAAAAAAATAATTTTAACTATATATAAAA

2025 ATGTATAATTTTTTGTCTGAGAATAGGAGGAACAATATATTTAAGAAGGAATCTTTGCTT

2085 GCTTAGGATAGCTTCACATCATACTTTTCCCACTACATAGGTAATAGGAAGGCATATGCT

2145 CTATTCCTTCATAACTTACTCTTGGTATTTCTTATCCTAATCGCCAAAAAAAGAGAGTAT

2205 AATTTTTATTTATAACACACTTTTTTATTTCCTATACAAGAATAAGTTGATTTTTCCATT

2265 TAAGTATAAACATCGAAACTTTTAGAGCGACTCTATAAGAGACTGCCCAATTTCATTGGG

2325 ATTCTACAAGATATTTTCATTGATTCTTGGAGACTACTTAATCT 2368            3'
```

FIG.6(Cont.)

```
  1  ATACCTTCTTCTCTCATCCTTCATAGCTAATAATATCATCTTCCCTG
 54  TTTTTACTGAACTGGCTAACTCTCAGTTAACTCTGGAGGAAACAACAAAC

98  AAAGGGTGGTGCTCGCCCTATATGAAGCCTTGAGCTCACACGACGTCGT  147
     ||||||||||||||||||||||||||||||||||||||||||||||||
  1  AAAGGGTGGTGCTCGCCCTATATGAAGCCTTGAGCTCACACGACGTCGT   50

148  TCAGGTCCAGAAACTCCTGGCCTCCGACCTCGAGTGGTGGTTCCATGGTC  197
     ||||||||||||||| ||||||||||||||||||||||||||||||||
 51  TCAGGTCCAGAAACTACTGGCCTCCGACCTCGAGTGGTGGTTCCATGGTC  100

198  CTCCTTCTCATCAATTTTTGATGCAAATACTCACCGGCACTGCTAAATTC  247
     ||||||||||||||||||||||||||||||||||||||||||||||||
101  CTCCTTCTCATCAATTTTTGATGCAAATACTCACCGGCACTGCTAAATTC  150

248  GATAACGCCTCTTTTCAATTCCTTCATAAGACCATTGACGTATTCGGTTC  297
     |||||||||||||||||||||||||||||||||||||||||||||||||
151  ACGCCTGGACTGTTACAGATGGGGTAATTACCCAGGTTAGGGAGTATTTC  200

298  CGTTGTTCTCGTCGAAGGCTGTGACCCGACCCGATCTATTACTTGGGTTC  347
     |||||||||||  ||||| ||||||||| |||||||||||||||||||
201  CGTTGTTCTCGTTGAAGGTTGTGACCCAACCCGATCTATTACTTGGGTTC  250

348  ACGCCTGGACTGTTACGGATGGGGTAATTACCCAGGTTAGGGAGTATTTC  397
     ||||||||||||||| ||||||||||||||||||||||||||||||||
251  ACGCCTGGACTGTTACAGATGGGGTAATTACCCAGGTTAGGGAGTATTTC  300

398  AATACCTCACTTACTGTCACCCGTTTTGGGAAATCGGATATTTCCTCAAT  447
     |||||||||||||||||||||||||||||||||||||||||||||||||
301  AAtACCTCACTTACTGTCACCCGTTTTGGGAAATCGGATATTTCCTCAAT  350

448  TACGACTCTGCATTGCCCATCTGTTTGGGAGAGTAGCTTACCAAATCGGG  497
     |||||||||||||||||||||||||||||||||||||||| |||||||
351  TACGACTCTGCATTGCCCATCTGTTTGGGAGAGTAGCTTACCTAATCGGG  400

498  TCGGAAAATCTGTTCCGGGTCTTGTATTGGCTCTATAAGAAACGACCCGA  547
     |||||||||||||||||||||||||||||||||||||||||||||||||
401  TCGGAAAATCTGTTCCGGGTCTTGTATTGGCTCTATAAGAAACGACCCGA  450
```

FIG.9

```
548  TTTGTGGCTGGCGTTATATCTTGTGTCTAGTAGgATGTAAGATTAACGCG  597
     |||||  |||||||||| ||||||||||||||| ||||||||||||||||
451  TTTGT.GCTGGCGTTGTATCTTGTGTCTAGTAGGATGTAAGATTAACGCG  499

598  GCTGGTTTGGGATTCTGTTGCTGCT.......GTTTGGTTTGTTTTTATT  640
     |||||||||||||||||||||||||       ||||||||||||
500  GCTGGTTTGGGATTCTGTTGCTATTTGGTTTTGATTTGGTTTGTTTTATT  549

641  TTTTAAGTTGGGATTTGTGTTCTGTTTATTATTTGTTGTTGTGATTGAGT  690
     ||||||||||||||||||||||||||||||||||||||||||||||||||
550  TTTTAAGTTGGGATTTGTGTTCTGTTTATTATTTGTTGTTGTGATTGAGT  599

691  TAAAGAAGGGGCCAATGATAATTGGATATACCTTTCTACTCAATAgATTG  740
     ||||||||||||||||||||||||||||||||||||||||||||| ||||
600  TAAAGAAGGGGCCAATGATAATTGGATATACCTTTCTACTCAATAGATTG  649

741  TCTAATTATGTGTTGGTTTGCAATAAAAAGCATATTGATTGGCTGTTTAC  790
     ||||||||||| |||||||||||||||| |||||||||||||||||||
650  TCTAATTATGTATTGGTTTGCAATAAAAAgCATATTGATTGGCTGTTTAA  699

791  AAAATGTGTATATTTTTCAATTTGGTATTGCTTCTTGTTTTCAACGAATG
     ||||
700  AAAAAAAAAAAAA  711
```

FIG.9(Cont.)

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 12 bases
( B ) TYPE: nucleic acids
( C ) STRANDEDNESS: single
( D ) TOPOLOGY: linear ( i i ) MOLECULE TYPE: cDNA
( A ) DESCRIPTION ( i i i ) HYPOTHETICAL: NO ( i v ) ANTI-SENSE: NO ( v i ) ORIGINAL SOURCE: cDNA LIBRARY
( A ) ORGANISM: SOLANUM TUBEROSUM
( B ) STRAIN: GRANOLA ( x i ) SEQUENCE DESCRIPTION: SEQ ID NO: 1:

TTTTTGATGC AA ( 2 ) INFORMATION FOR SEQ ID NO:2:

( i ) SEQUENCE CHARACTERISTICS:
( A ) LENGTH: 12 BASES
( B ) TYPE: NUCLEIC ACID
( C ) STRANDEDNESS: single
( D ) TOPOLOGY: linear ( i i ) MOLECULE TYPE: cDNA
( A ) DESCRIPTION ( i i i ) HYPOTHETICAL: YES ( i v ) ANTI-SENSE: NO ( i x ) FEATURE
( D ) OTHER INFORMATION: CONSENSUS SEQUENCE FOR PLANT
TRANSLATION START SITE.

( x ) PUBLICATION INFORMATION
( A ) AUTHOR: JOSHI
( B ) TITLE: AN INSPECTION OF THE DOMAIN BETWEEN PUTATIVE
TATA BOX AND TRANSLATION START SITE IN 79 PLANT GENES
( C ) JOURNAL: NUCLEIC ACIDS RESEARCH, 15:6643- 6653 (1987)

( x i ) SEQUENCE DESCRIPTION: SEQ ID NO:2:

TAAACAATGG CT ( 3 ) INFORMATION FOR SEQ ID NO:3:

( i ) SEQUENCE CHARACTERISTICS:
( A ) LENGTH: 13 BASES
( B ) TYPE: NUCLEIC ACID
( C ) STRANDEDNESS: SINGLE
( D ) TOPOLOGY: LINEAR ( i i i ) HYPOTHETICAL: YES ( i v ) ANTI-SENSE: NO ( i x ) FEATURE
( D ) OTHER INFORMATION: CONSENSUS SEQUENCE FOR PLANT TATA
BOX.

( x ) PUBLICATION INFORMATION
( A ) AUTHOR: JOSHI
( B ) TITLE: AN INSPECTION OF THE DOMAIN BETWEEN PUTATIVE
TATA BOX AND TRANSLATION START SITE IN 79 PLANT GENES
( C ) JOURNAL: NUCLEIC ACIDS RESEARCH, 15:6643- 6653 (1987)

( x i ) SEQUENCE DESCRIPTION: SEQ ID NO:3:

TCACTATATA TAG ( 4 ) INFORMATION FOR SEQ ID NO:4:

( i ) SEQUENCE CHARACTERISTICS:
( A ) LENGTH: 661 BASES
( B ) TYPE: NUCLEIC ACID
( C ) STRANDEDNESS: SINGLE
( D ) TOPOLOGY: LINEAR ( i i ) MOLECULE TYPE: cDNA ( i i i ) HYPOTHETICAL: NO ( x i ) SEQUENCE DESCRIPTION: SEQ ID NO:4:

AAAGGGGTGG TGCTCGCCCT ATATGAAGCC TTGAGCTCAC ACGACGTCGT           50

-continued

| | | | |
|---|---|---|---|
| TCAGGTCCAG | AAACTACTGG | CCTCCGACCT CGAGTGGTGG | TTCCATGGTC | 100 |
| CTCCTTCTCA | TCAATTTTTG ATG CAA ATA CTC ACC GGC ACT GCT | | 141 |
| AAA TTC GAT AAC GCC TCT TTT CAA TTC CTT CAT AAG ACC ATT | | | 183 |
| GAC GTA TTC GGT TCC GTT GTT CTC GTT GAA GGT TGT GAC CCA | | | 225 |
| ACC CGA TCT ATT ACT TGG GTT CAC GCC TGG ACT GTT ACA GAT | | | 267 |
| GGG GTA ATT ACC CAG GTT AGG GAG TAT TTC AAT ACC TCA CTT | | | 309 |
| ACT GTC ACC CGT TTT GGG AAA TCG GAT ATT TCC TCA ATT ACG | | | 351 |
| ACT CTG CAT TGC CCA TCT GTT TGG GAG AGT AGC TTA CCT AAT | | | 393 |
| CGG GTC GGA AAA TCT GTT CCG GGT CTT GTA TTG GCT CTA | | | 432 |
| TAAGAAACGA | CCCGATTTGT | GCTGGCGTTG | TATCTTGTGT CTAGTAGGA | 482 |
| TGTAAGATTA | ACGCGGCTGG | TTTGGGATTC | TGTTGCTATT TGGTTTGAT | 532 |
| TTGGTTTGTT | TTTATTTTTT | AAGTTGGGAT | TTGTGTTCTG TTTATTATTT | 582 |
| GTTGTTGTGA | TTGAGTTAA | AGAAGGGGCC | AATGATAATT GGATATACCT | 632 |
| TTCTACTCAA | TAGATTGTC | TAATTATGTA | TTGGTTTGCA ATAAAAAGCA | 682 |
| TATTGATTGG | CTGTTTAAA | AAAAAAAAA A | | 713 |

(5) INFORMATION FOR SEQ ID NO:5:

( i ) SEQUENCE CHARACTERISTICS:
( A ) LENGTH: 1268 bases
( B ) TYPE: nucleic acid
( C ) STRANDEDNESS: single
( D ) TOPOLOGY: linear ( i i ) MOLECULE TYPE: genomic ( i i i ) HYPOTHETICAL: no ( x i ) SEQUENCE DESCRIPTION: SEQ ID NO:5:

| | | | | |
|---|---|---|---|---|
| AAATTTTATA | CATACATACA | AACACAATCA | TTGATACATA | ACAATGATGT | 50 |
| ACATATATAC | AATTATCTAA | CCGATATATA | TATATATATA | TATATATATA | 100 |
| TATATCACCT | CTCTCCACTC | TCTGCCCTCT | CTTCATTCTC | TCCCAATCTC | 150 |
| GCTCACCACT | CTAGCCTAAC | ATAGAGAACA | TATACATATA | CAAACACAAT | 200 |
| TTTCATAGAC | ACAAATGGAA | TTAATACCTG | ATTTATATAA | ATCGCCGTGA | 250 |
| TTTATACAAA | TCAGATGCTC | CATAACAAAC | ATAATTTGAC | CCATGGAGTG | 300 |
| CATATAACAA | AATTGTAGCT | ATAGAACGCT | AATATGTTTT | TCTTAATCTT | 350 |
| TGTTATTCCT | AAAATTTACT | CATAATAATA | CTCTTTATAA | AAGCATAAGC | 400 |
| TGGTTTGGTT | TAGGGTTAGA | GTATTCTCTA | AAAATTCTAA | TTGAAATCAA | 450 |
| ATACATCTTA | TAGAATCCAA | ATTAGAATTG | AACACGTCTT | GTAGAGTCCC | 500 |
| ATAAATTTTT | AATGTCTACA | ATGTAATATC | GTTAAAATAT | TTTAATATCT | 550 |
| TGTTGAAATA | TAATTTTTTA | TTTAGTAAAA | TAATATGAGA | ATTAATTTTT | 600 |
| TTTATTAATC | TTCACAACTA | TGATTTTTTT | AAAATTTCAT | GTAAATATAT | 650 |
| GGGCTAAGAT | TGTGAGCCAA | CTGGTCAAAA | CTCAAAGTT | AGTCGAGTTT | 700 |
| GAATGAAGTT | AAAATTAAAA | GTATTGTTGT | CATAACTCAT | ATGTTGCAAG | 750 |
| TTGCAACTGT | GTGTATAAGG | TCAAAAAAGG | TATGCTTGAA | AGTTGAAACT | 800 |
| TTAGATATGA | CGATCATCTT | CGTGGGCCCT | ACCTAAAATA | AAACGTCTCT | 850 |
| TCATCATCCG | AATATCACAT | CATCACGTAA | TCCCCGAGCA | CGTGGAATGG | 900 |
| CGCGTAAATA | TCATGTCGCC | CTTTAAACCT | AAATACACCT | ACTATTCACC | 950 |

```
TATAATTTCC  AAACTACCCT  TCCAACGTCC  CTATATATTC  CCCACATCAC   1000
ACCTCTTTCT  TCATTACCTA  CCATACCTTC  TTCTCTCATC  CTTCATAGCT   1050
AATAATATCA  TCTTCTGTTT  TTACTGAACT  GGCTAACTCT  CAGTTAACTC   1100
TGGAGGAAAC  AACAAACAAA  GGGGTGGTGC  TCGCCCTATA  TGAAGCCTTG   1150
AGCTCACACG  ACGTCGTTCA  GGTCCAGAAA  CTCCTGGCCT  CCGACCTCGA   1200
GTGGTGGTTC  CATGGTCCTC  CTTCTCATCA  ATTTTTG ATG CAA ATA CTC  1249
ACC GGC ACT GCT AAA TTC GAT AAC GCC TCT TTT CAA TTC CTT      1291
CAT AAG ACC ATT GAC GTA TTC GGT TCC GTT GTT CTC GTC GAA      1333
GGC TGT GAC CCG ACC CGA TCT ATT ACT TGG GTT CAC GCC TGG      1375
ACT GTT ACG GAT GGG GTA ATT ACC CAG GTT AGG GAG TAT TTC      1417
AAT ACC TCA CTT ACT GTC ACC CGT TTT GGG AAA TCG GAT ATT      1459
TCC TCA ATT ACG ACT CTG CAT TGC CCA TCT GTT TGG GAG AGT      1501
AGC TTA CCA AAT CGG GTC GGA AAA TCT GTT CCG GGT CTT GTA      1543
TTG GCT CTA TAAGAAACGA CCCGATTTGT GGCTGGCGTT ATATCTTGTG      1592
TCTAGTAGGA TGTAAGATTA ACGCGGCTGG TTTGGGATTC TGTTGCTGCT       1642
GTTTGGTTTG TTTTTATTTT TTAAGTTGGG ATTTGTGTTC TGTTTATTAT       1692
TTGTTGTTGT GATTGAGTTA AAGAAGGGGC CAATGATAAT TGGATATACC       1742
TTTCTACTCA ATAGATTGTC TAATTATGTG TTGGTTTGCA ATAAAAAGCA       1792
TATTGATTGG CTGTTTACAA AATGTGTATA TTTTTCAATT TGGTATTGCT       1842
TCTTGTTTTC AACGAATGAC GATGGATACC GTGGAAACAA TTTCATTGAA       1892
AGGCAAATCT TATTATTAAT GATGGAATCA GAATTTTTAT TATGAGGTTT       1942
AAATAATTAA ACATATAAAA TAGTTAAATG AGGTTCGAAA TCTATATAAT       1992
GCATAAAAAA ATAATTTTAA CTATATATAA AAATGTATAA TTTTTTGTCT       2042
GAGAATAGGA GGAACAATAT ATTTAAGAAG GAATCTTTGC TTGCTTAGGA       2092
TAGCTTCACA TCATACTTTT CCCACTACAT AGGTAATAGG AAGGCATATG       2142
CTCTATTCCT TCATAACTTA CTCTTGGTAT TTCTTATCCT AATCGCCAAA       2192
AAAAGAGAGT ATAATTTTTA TTTATAACAC ACTTTTTTAT TTCCTATACA       2242
AGAATAAGTT GATTTTTCCA TTTAAGTATA AACATCGAAA CTTTTAGAGC       2292
GACTCTATAA GAGACTGCCC AATTTCATTG GGATTCTACA AGATATTTTC       2342
ATTGATTCTT GGAGACTACT TAATCT                                 2368
```

WOUND-STIMULATED DNA-SEQUENCE FROM SOLANUM TUBEROSUM AND ITS USE

This application is a continuation of application Ser. No. 07/690,946, filed on May 2, 1991, now abandoned.

BACKGROUND OF THE INVENTION

The invention relates to wound-stimulated DNA from *Solanum Tuberosum* as well as parts thereof, the use of such for the production of gene products in higher plants using wound or pathogen attack, DNA-propagation vectors containing the same, and plants or plant parts containing the same.

It is known that the mechanical injury of plant tissue can cause morphological and physiological changes. Thus, the activity of various enzymes increases after the wounding, for example of phenylalanine-ammonialyase and peroxidases in potato tubers, extensin in the storage tissue of carrots, fatty acid synthetase in potato tubers and proteinase-inhibitors in tomato and potato leaves. For some of these enzymes, the increase in activity is associated with increased mRNA amounts. One of the best understood wound-induced genes is the proteinase-inhibitor in tomatoes and potatoes; in wounded leaves, the mRNA for this gene is significantly increased.

The wound-induced development of genes in plants is of fundamental interest, because in this area the promoters that become active are capable of specifically activating the corresponding structure gene after wounding. Promoters of this kind in connection with other genes which, for example, code for resistance, or code substances that are effective as antibiotics, or promote the healing of wounding, are naturally of great economic interest, if they can be inserted into the genetic material of other plants.

It has now been found that relatively high concentration of induced mRNA are specifically present in wounded and/or microbially attacked potato plants. This mRNA can be isolated and characterized. It does not appear in healthy, uninjured plants.

SUMMARY OF THE INVENTION

Accordingly, the invention has as an object a DNA-sequence from *Solanum Tuberosum*, which is stimulated through wounding and/or infection with pathogenic microbes, as well as the promoter part and the structural gene part. Further, the invention has as its object the use of this DNA-sequence for the expression of gene products in higher plants after wounding and/or pathogenic attack.

Furthermore, the invention has as its object DNA-propagation vectors into which DNA-sequences have been inserted, such sequences being defined above. Finally, the invention has as a further object plants or plant materials which contain such a DNA-sequence.

The expression "transcriptionally active region" of a gene, of its promoter part and structural gene part, is to be understood to refer to those nucleotide-sequences which are unconditionally necessary in the promoter region of the gene for the activation of the structural gene part and in the structural gene part for the expression of an effective or active gene product.

The expression "structural gene" is to be understood to refer not only to the DNA-sequence from *Solanum Tuberosum* in systems homologous to that herein described but also structural genes from other sources, thus from heterologous systems. An example would be the CAT-, NPT- and GUS-structural genes, which can be fused with the wound-stimulated promoter described herein, and can be used for the development of the respective structural gene in potato or foreign plants.

The propagation vectors can be provided by any suitable DNA-molecules which can be introduced into the final bacterium. Typically, these would be plasmids as are more fully described in the disclosure. The insertion techniques are known to the person skilled in the art.

The bacteria for the uptake and release of the propagation vectors can be constituted by bacteria of the genus Agrobacterium, in particular *Agrobacterium tumefaciens* and *Agrobacterium rhizogenes*.

EP-A 122,791 describes a DNA-propagation vector which contains T-DNA with a plant gene inserted therein. This plant gene consists of a plant promoter and a plant structural gene, wherein the plant promoter is joined to the 5'-end of the plant structural gene, and the plant structural gene is located behind the plant promoter in the transcription direction. EP-A 122,791 provides a detailed description of processes and steps for the insertion of genetic material in DNA-propagation vectors, to which reference is now expressly made.

Research has shown that Erwinia-bacteria are latent in potato plants (*Solanum tuberosum*) and that they will preferentially attack the stem and the tubers of potatoes only after tissue has been wounded. This was induced in potato tubers of the species *Datura*, by slicing the tuber into discs and simultaneously incubating with *Erwinia carotovora* of the species *atroseptica*. As expected, these tubers exhibited a severely macerated surface after eighteen hours of incubation. The isolation of mRNA from the tissues lying under the maceration was not possible with standard methods. The reasons for this were a high contamination of the RNA with polysaccharides, poor precipitation and redissolvement of the RNA, a high level of RNA degradation, a small yield of RNA and substantial labor and material expenditures. By variations and new combinations of existing methods, however, it was possible to develop a technique by which large amounts of non-degraded RNA could be obtained with relatively small material and time expenditures, even from tissues containing polysaccharides. (Logemann et al, Anal. Bioch. 163, 16, 1987).

On the basis of cleaned polyA+RNA from wounded tubers of the potato species *granola*, incubated with Erwinia, a cDNA-bank was built up. Using differential colony hybridization techniques of 4000 cDNA-clones were hybridized with radioactively labelled RNA from non-wounded and Erwinia-wounded tubers. Two clones were identified, here named wun1 and wun2, of which the complementary mRNA were induced by wounding of tubers of various tetraploidal potato species as well as the haploidal species AM 80/5793. Wun1-mRNA accumulated within thirty minutes after mechanical wounding of a tuber, and is thus involved in the primary processes induced by wounding, whereas wun2 was induced 3.5 hours after wounding. Twenty-four hours after wounding, both clones showed even higher concentration of m-RNA. If in addition to the mechanical wounding, the tuber is incubated with *Erwinia carotovora* of the species *atroseptica*, no alteration is found in the expresion pattern. Altogether, the expression studies with tubers reveal that wun1-mRNA and wun2-mRNA represent genes which are not Erwinia-specifically induced, but are stimulated by all processes which result in the destruction of the tuber tissue.

Wun1-mRNA accumulates in large quantities in wounded potato tubers (quantity-wise comparable with proteinase-inhibitor II-mRNA in non-wounded potato tubers, compare Sanchez-Serrano et al, Mol. Gen. Genet. 2032, 15 (1986)); whereas in non-wounded tubers, it is not detectable. It first appears thirty minutes after wounding with a maximum between the fourth and twenty-fourth hour after injury. In smaller amounts, it was also detectable even after forty-eight hours.

The accumulation of wun1-mRNA and wun2-mRNA after wounding is not limited to the tuber, but also takes place in the leaves, stems and roots of various tetraploidal potato plants with comparable kinetics and intensity.

In contradistinction to wun2-mRNA, wun1-mRNA is induced in leaves also in the absence of wounding, when the leaves are sprayed with compatible phytophtora infestans spores. This result shows that wun1 can be induced not only through mechanical wounding, but also through the presence of (fungoid) pathogens.

There were differences in the development of the wun1-gene, according to whether the tubers were wounded under aerobic conditions (tuber slices were sprayed with P-buffer and incubated for eighteen hours, then exposed to the air) or were wounded under anaerobic conditions (tuber slices were dipped in P-buffer and in this oxygen-starved condition incubated for eighteen hours). wun1-mRNA expression was significantly higher in aerobically wounded tubers than in the corresponding anaerobic situation.

For the use of promoters for the expression of genes in accordance with the invention, it is important whether the detectable wun1-mRNA or wun1-mRNA arises through a new synthesis (transcriptional regulation), or is constitutively expressed and stabilizes only in the case of a wounding (post-transcriptional regulation).

"Run-off" transcription tests were able to demonstrate transcriptional regulation for both wun1 and wun2, which means that the promoters of these genes are responsible for the new synthesis in case of an wounding.

Using known techniques, a series of wun1-homologous cDNA-clones were obtained from the tetraploidal potato "granola", from which some of them were sequenced. By cloning wun1-25A2 in M13mp19-phages in both orientations and partial exonucleaseIII digestion, the nucleotide sequence was analysed in both directions according to the dideoxy method.

BRIEF DESCRIPTION OF THE FIGURES

FIG. 2 shows the nucleotide sequence of the cDNA clone wun1-25A2.

FIG. 5 shows the result of deletion analysis of clone wun1-85 in schematic form.

FIG. 6 shows the nucleotide sequence of the wun1 promoter region and coding region from clone wun1-85.

FIG. 9 gives the sequence comparison between the cDNA clone wun1-25A2 and the genomic clone wun1-85.

DETAILED DESCRIPTION OF THE INVENTION

Figure 1:
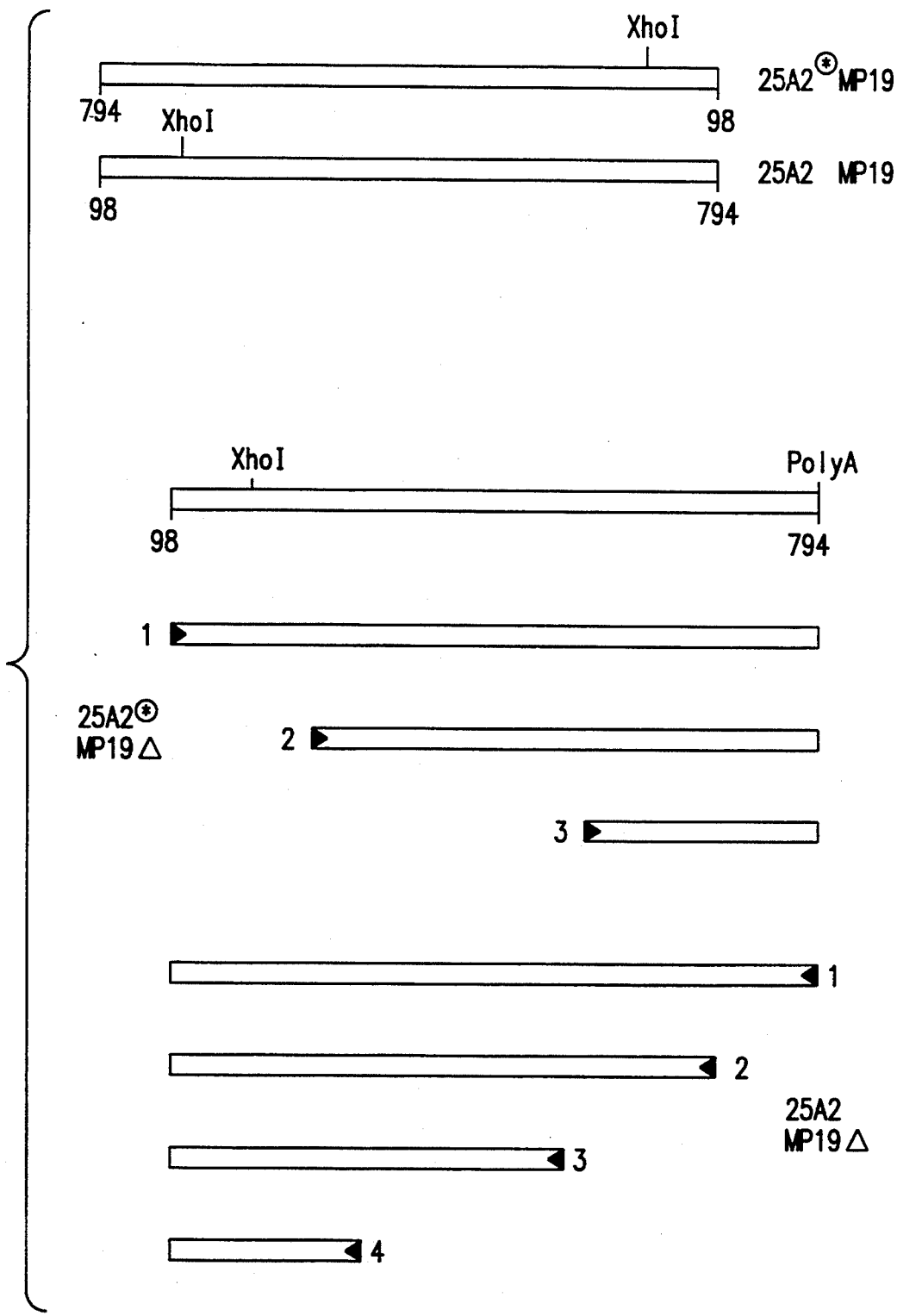
FIG. 1 shows the relative sizes of the clones used for sequencing.

FIG. 1 shows the relative sizes of the clones used for sequencing. The clone wun1-25A2 has been cloned in two orientations in the PstI-site, which, in respect to the position of the asymmetric XhoI section position are called 24A2*MP19 and 25A2MP19. Using successive exonucleaseIII-digestions, it was possible to obtain deletion clones of different sizes, which were available as clone 25A2*MP19delta 1–3 and 25A2MP19delta 1–4 for sequencing.

FIG. 2 shows the nucleotide sequence of the cDNA-clone-wun1-25A2. Alternative open reading frames are underlined.

The size of the cDNA-clone-wun1-25A2 is 711 bp. At the 3-end is a poly-A tail of 14 bp (position 697–711). The largest open reading frames extends over 105 aminoacids (position 121–438). Further, in 5'-position are two short open reading frames which code for three amino acids in position 23 and code for eight amino acids in position 95 (underlined). The last two mentioned open reading frames differ however from that which codes the 105 amino acids. By referring back to the genomic sequence data (FIG. 6) the reading frame coding for 105 amino acids is related to the wun1-protein. The translational start point of the wun1-protein TTTTTGATGCAA fits only to a lower extent the consensus sequence for plant translation start TAAACAATGGCT, as reported by Joshi, Nuc. Acids Res. 15, 6643, (1987).

Figure 3:
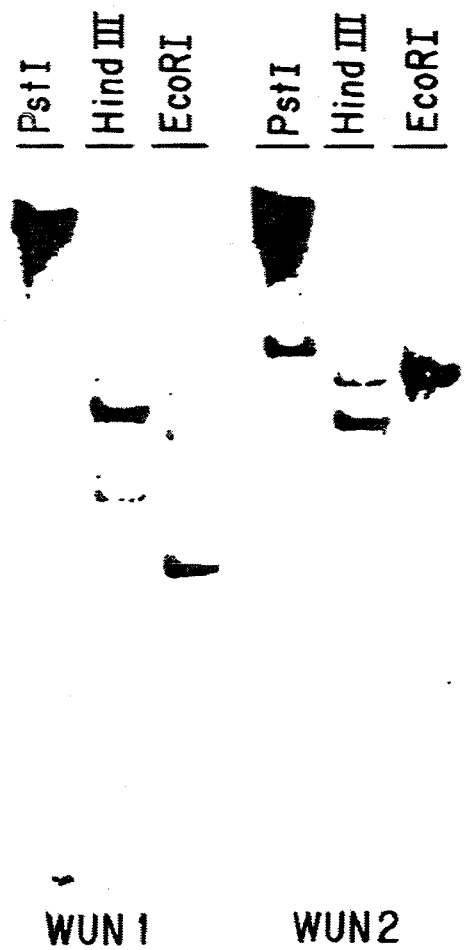
FIG. 3 shows the result of "Southern blot" analysis of wun1 and wun2 cDNA.

Investigation of the genomic organization of the gene coding for wun1-mRNA in the haploid potato line AM80/5793 shows that this gene is available in only a limited number of copies. The hybridization of radioactively-marked wun1-cDNA against HindIII-, PstI- and EcoRI-digested leaf-DNA leads, in the "Southern Blot" analysis, to the definition of one strong and one or two weak bands. The result of the "Southern Blot" analysis of wun1- and wun2-cDNA is illustrated in FIG. 3.

For the haploid potato line AM80/5793, the "Southern Blot" analysis was able to identify only a few genes responsible for the development of wun1- and wun2-mRNA. The likelihood of obtaining an active gene and no inactive pseudogene was particularly high here.

The presence of only one defined band in the "Southern Blot" of the haploid potato line points to a limited number of genes per genome. If this is considered along with high and wound-specific expression of wun1-mRNA in the haploid line and transcriptional regulation, highly active genes become likely.

To build up a genomic bank, 10 micrograms of EcoRI-digested DNA from AM80/5793 was ligated with EcoRI-digested EMBL4-arms, and plated out on a C600-bacteria-containing medium. Approximately 500,000 plaques were obtained which, considered statistically, represent the genome of the potato. After the transfer of these plaques to nitrocellulose, plaque hybridization techniques with radioactively labelled wun1-cDNA permitted the identification and purification of the genomic clones wun1-22 and wun1-85.

The isolation of recombinant EMBL4-DNA from wun1-22 and wun1-85, as well as the restriction mapping and hybridization thereof with radioactive wun1-cDNA gave the following organization.

The wun1-cDNA-equivalent fragment in wun1-85 has a size of 4 Kb. This exactly corresponds with the fragment size (hybridizing with wun1-cDNA) of EcoRI-digested DNA from the haploidal potato. On the basis of the asymmetric XhoI-site in the 5'-region of the cDNA-clone, the orientation of the gene in the 4 Kb fragment could be established. According to this, a roughly 1 Kb sized promoter region lies upstream of the wun1-gene, whereas a rougly 2 Kb sized non-homologous portion is located 3' from the gene. The 8 Kb-large EcoRI fragment, also contained in wun1-85, could not be used for further analysis of the wun1-gene. On the basis of the total digestion of the potato DNA with EcoRI, it is likely that during ligation, two fragments that did not belong together were inserted into the EMBL4-vector, these fragments being not functional related with each other.

Figure 4:
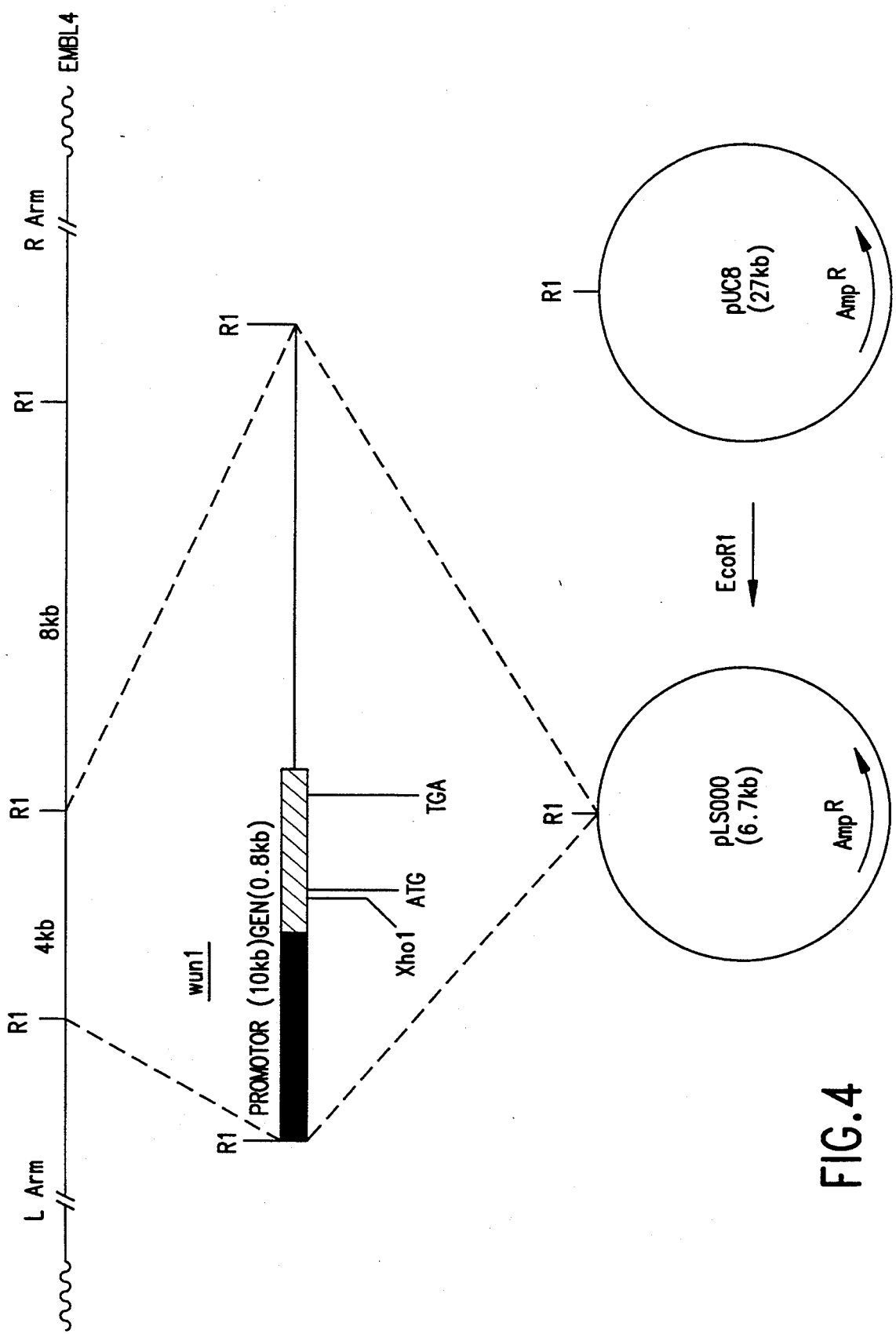
FIG. 4 shows the arrangement of wun1 in the genomic clone wun1-85.

FIG. 4 shows the arrangement of wun1 in the genomic clone wun1-85. Located on the 4 Kb-large EcoRI fragment of the genomic clone wun1-85 are 1.0 Kb of wun1-promoter, 0.8 Kb of the wun1 gene and 2.0 Kb of the 3'-end.

Since in the restriction pattern no differences emerged between wun1-85 and wun1-22, for further analysis the 4 Kb fragment of wun1-85, was ligated into EcoRI digested pUC8 (see FIG. 4). For the sequencing of the wun1 promoter as well as the wun1 gene, there followed a further recloning of the 4 Kb fragment in the EcoRI site of M13mp18. The determination of its orientation was carried out with control digestions using at the asymmetrically located XhoI-site. The clones 85*mp18 and 85mp18 represent both orientations of the fragment. The digestion of these plasmids with SphI and XbaI made it possible, with the help of exonucleaseIII, to successively digest the 3'-end of the wun1-gene of the clone 85mp18, and the 5'-end of the wun1-gene of the clone 85*mp18.

FIG. 5 shows the result of the deletion analysis of clone wun1-85 in schematic form.

The resulting deletion clone with different fragment sizes was used for the sequencing. Generally, it was possible to sequence the entire wun1-gene bidirectionally, and, in addition, to analyze about 400 bp of the 3'-end unidirectionally.

Figure 7:
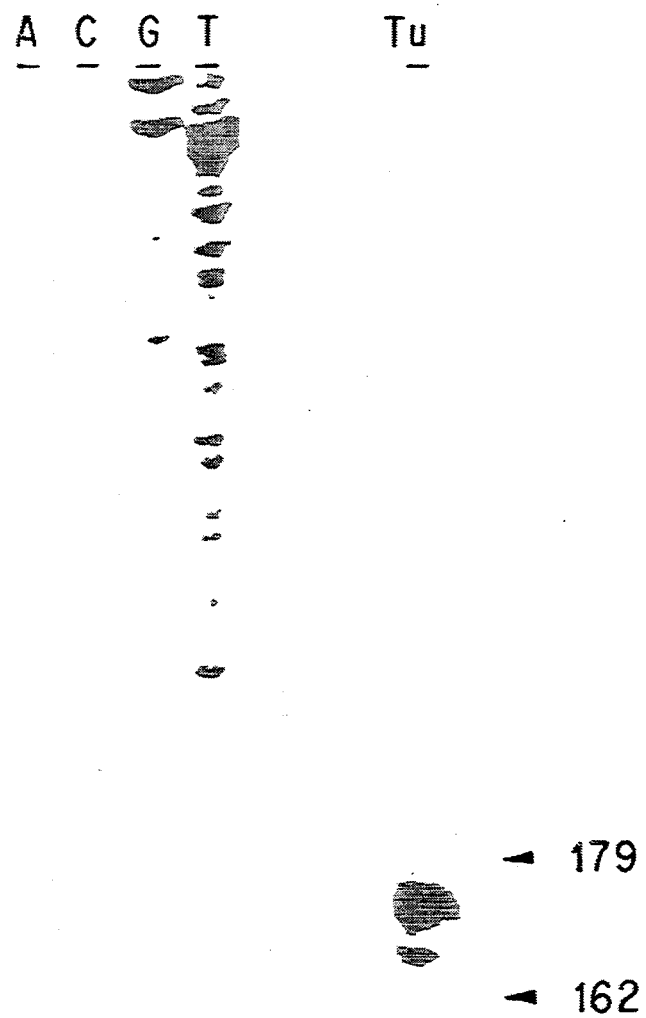
FIG. 7 shows the determination in size of the S1-protected fragment of the wun-1 gene.

FIG. 6 shows the nucleotide sequence of the wun1 promoter and gene from wun1-85. The CAAT-box, TATA-box and Poly-A signal are indicated, and the transcriptional start- and stop site are marked with arrows. In order to identify the precise transcriptional start site of the wun1-gene, the method of S1-nuclease-mapping was used. FIG. 7 shows the determination of the size of the S1-protected fragment of the wun1 gene. The hybridization with wun1-mRNA of the region in pLS000 lying 5' from the XhoI site leads to a 162-179 bp long DNA-RNA-hybrid (TU), which is protected from the single-strand specific S1-nuclease. The actual transcriptional start site thus lies 162-197 bp 5' from the XhoI section location (A,C,G,T=the sequence arrangement for the sizing the DNA fragment).

If one begins with the longest obtained fragment, then the transcription start begins 179 bp upstream from the XhoI-position, i.e. with the sequence ACCATAC. This sequence agrees fully in the central region (CAT) with the concensus sequence or transcription start CTAATCA, discovered by Joshi et al (1987). From the position of the transcription start, further information is available (see FIG. 6):

(1) At position 33, as seen from the transcription start, a TATA-box CTATATATT is found which agrees well with the concensus sequence TCAC-TATATATAG, as described by Joshi et al (1987).
(2) The CAAT-box in the region between −60 and −80, described by Benoist et al, Nuc. Acids Res. 8, 127–142 (1980), is found in position −58 (CAAACT) in the wun1-promoter.
(3) The 5'-untranslated region of the wun1-gene has a size of 217 bp and, therefore, is relatively large.
(4) The wun1-mRNA coded gene is 794 bp in size, which very closely corresponds to the size of wun1-mRNA, on the basis of the "Northern-Blot" analysis.
(5) 97 bp of the 5'-untranslated region of the wun1 gene are missing in the cDNA-clone, wun1-25A2.
(6) Aside from the open reading frame already determined in the cDNA-clone, no others were found in the 5'-untranslated region of the genomic clone.
(7) The wun1-gene contains no introns.

Figure 8:
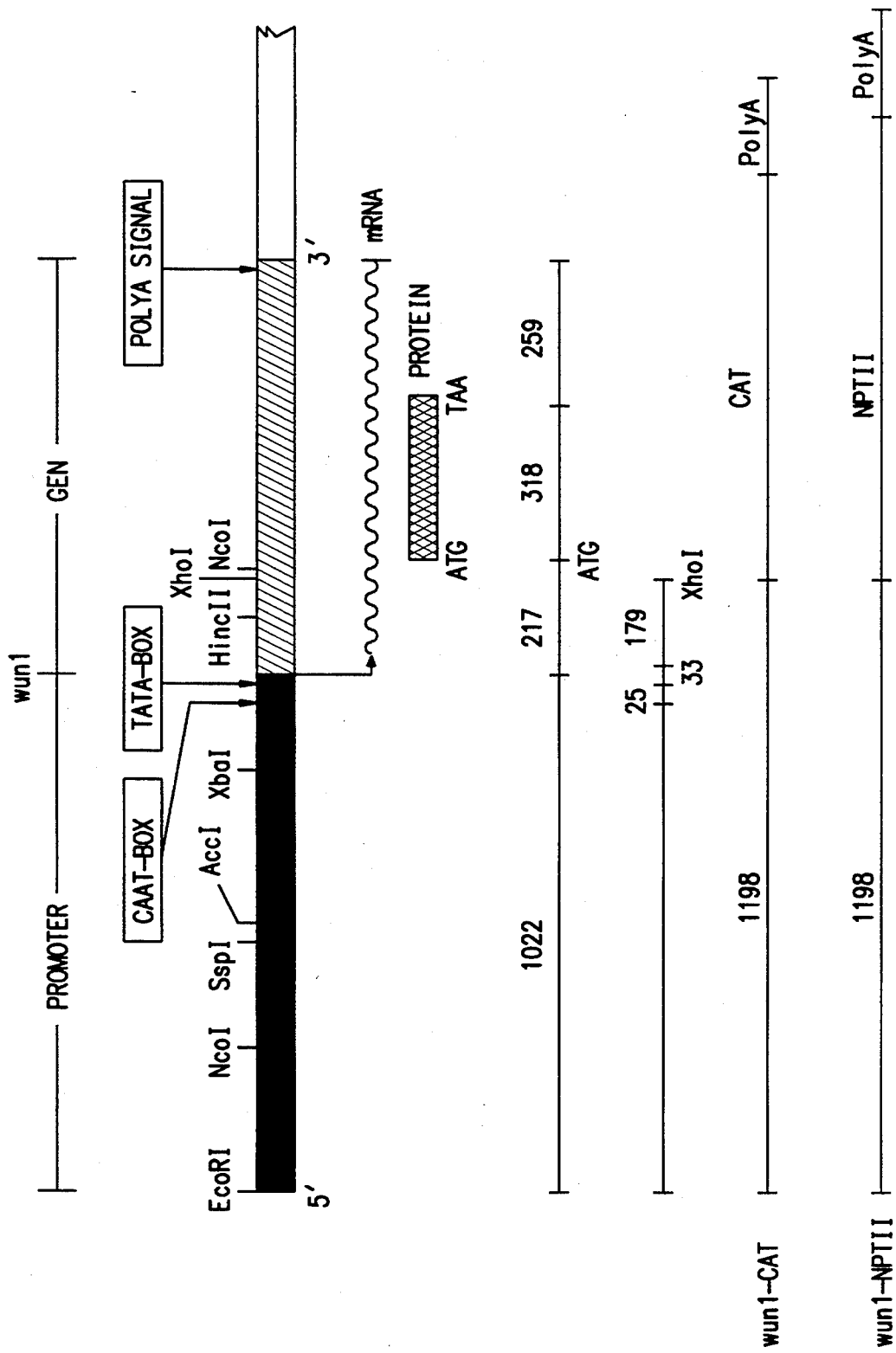
FIG. 8 shows the arrangement and positions of important regions in the wun-1 gene.

FIG. 8 shows the arrangement and position of important regions in the wun1-gene. The wun1-promoter is marked in black, while the wun1-gene is hatched. The important recognition sequences are boxed. The mRNA is shown by a sinuous line, whereas the protein coding region is marked with Xes. The sizes of the individual regions are given in base pairs (bp).

FIG. 9 gives the sequence comparison between the cDNA-clone wun1-25A2 and the genomic clone wun1-85. 2368 bp of the genomic clone wun1-5 were compared with 711 bp of the cDNA clone wun1-25A2. Homologous base pairs are marked by a vertical line. The missing nucleotides are shown by a period. The two arrows indicate the sequence of two 10-bp direct in the cDNA-clone.

Comparison analysis shows that the sequence of the genomic clone wun1-85 of the haploid potato AM80/5793 is up to 97% homologous with the sequence of the cDNA-clone wun1-25A2 of the tetraploidal potato "Granola". Altogether, 11 base pair changes were identified, of which five were located in the translated region. All five base pair changes in the translated region resulted in no alteration of the amino acid sequence. The additionally sequenced 400 nucleotides downstream of the transcription stop exhibit no remarkable regions.

The gene codes for a protein of 12000 Dalton, which size can be approximately determined in hybrid-released-translation-experiments. Computer evaluation relative to the amino acid combination of the wun1-protein indicates that a very hydrophilic protein. The amino acid sequence is seen in FIGS. 2 and 6.

The size of the wun1-protein, its hydrophilic characteristics, the wound-inducibility in various tissues and the inducibility by pathogens, can be concluded on the basis of the fact that it belongs to the PR-proteins. The name PR- or "Pathogenesis-Related"-protein includes proteins of various plants which are inducible, inter alia, by pathogen attack, and in some cases show Chitinase-activity or Glucanase-activity, i.e. the activity of enzymes which can destroy the cell walls of the fungus.

Using the agrobacterium-transformation system in transgenic tobacco plants, expression studies were possible on mRNA-level, since tobacco-mRNA cross-hybridizes only very weakly with wun1, and moreover does not possess any wun1-homologous 5'-ends, as can be gathered from S1-nuclease-mapping. Actually, a large quantity of approximately 800 bp-large wun1-mRNA was detected in transgenic tobacco plants in wounded leaves, which on the one hand shows an active wun1-promoter, and on the other indicates the use of the correct transcription start point.

A 4 Kb-fragment from pLS000, containing the wun1-promoter, the complete wun1-gene, and 2 Kb of the 3'-region of the gene (wun1-wun1), was cloned (pLS001) with its EcoRI-sites in the mobilization vector pMPK110, which is necessary for the *Agrobacterium tumefaciens* (At) transformation. After transfer to At3850$_{km}$, the tobacco line Wisconsin 38 (W38) was transformed with this Agrobacterium on leaf discs. The small callus appearing some three weeks after Kanamycin selection was regenerated to the complete plant (LS1) through the use of a shoot-induction medium.

Aside from the capability of growing on Kanamycin, plants transformed with 3850$_{Km}$ have the capability to synthesize nopaline, a property which distinguishes them from untransformed plants (Zambryski et al, EMBO J. 1 147-152 (1985)). Wun1-wun1 transformed plants, here called LS1-plants (4=LS1-4; 6=LS1-6), were characterized by a high level of nopaline. By contrast, no nopaline was detectable in untransformed plants. Kanamycin-resistant and nopaline-positive LS1-plants were transferred to the greenhouse and analyzed on the DNA- and RNA-planes.

Figure 10:
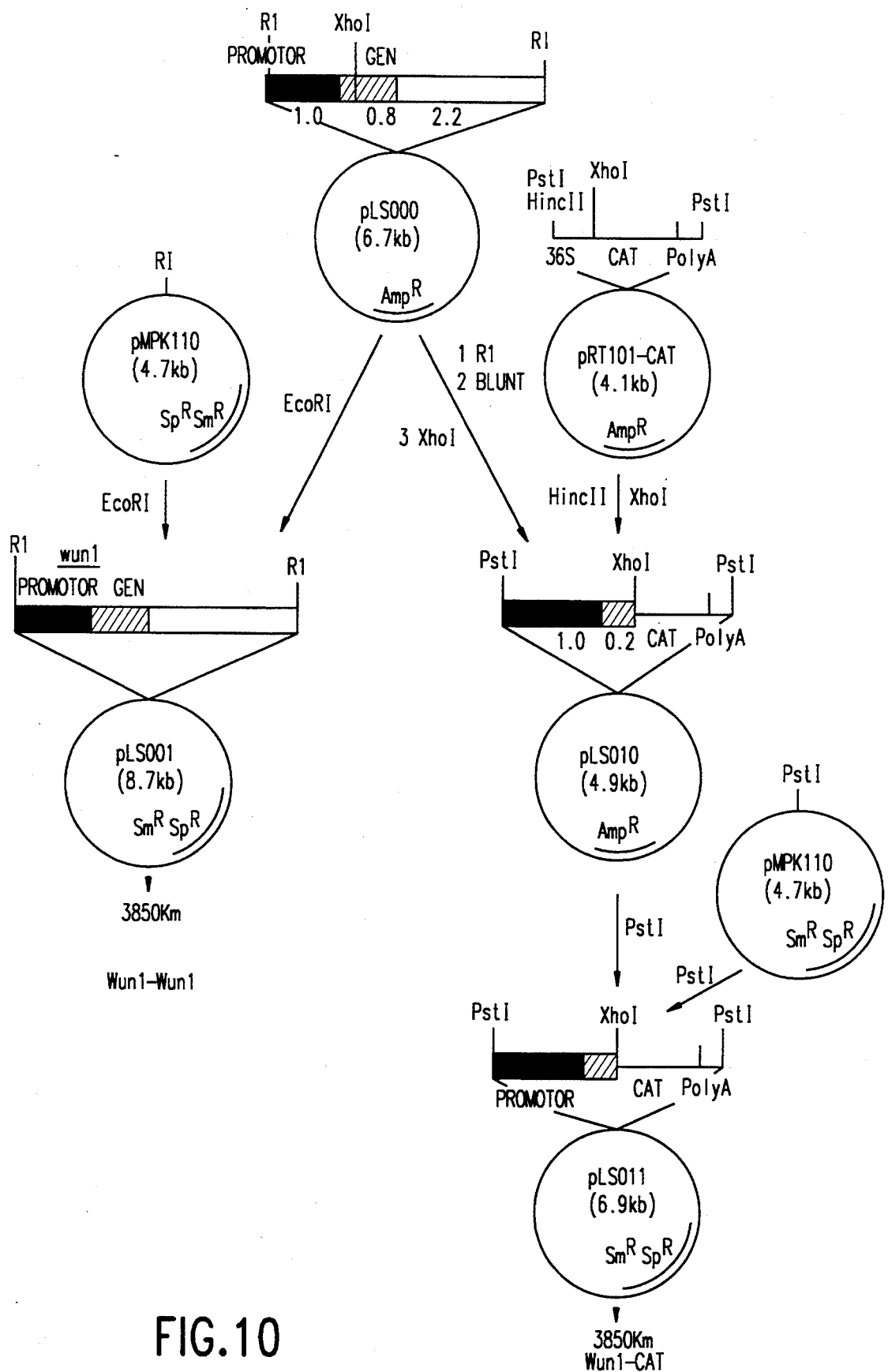
FIG. 10 shows the construction of the wun1-wun1 and wun1-CAT fusions.

FIG. 10 shows the construction of wun1-wun1-fusions and wun1-CAT-fusions which were utilized for expression studies on the basis of transient expression and stable transformations.

(1) The creation of the plasmid pLS001:

Beginning with the plasmid pLS000 (see FIG. 4), the 4 Kb-fragment which contains the wun1-promoter, the wun1-gene and 2 Kb of the 3'-end was cloned (pLS001) within the EcoRI-site of the vector pMPK110.

(2) Creation of the plasmid pLS011:

The wun1-promoter, as well as 179 BP of the 5'-untranslated wun1-gene region, were fused (pLS010) at the XHOI site with the CAT-gene inclusive 3'-end. Subcloning in the vector pMPK110 using PstI (pLS011) has the advantage that this plasmid can be used for transient studies in protoplasts and additionally can behave as a mobilization plasmid for the transfer of wun1-CAT-construction into the Agrobacterium 3850$_{Km}$.

The "Southern Blot" analysis of EcoRI-digested DNA from transgenic LS1-tobacco plants and untransformed W38-tobacco plants resulted in a positive hybridization through the use of $^{32}$P-radioactively labelled wun1-cDNA probe, both in the DNAs of untransformed plants and the DNAs of transformed plants. In both cases, a strong band and weak band were recognized. However, in the transgenic LS1-plants, there was additionally a 4 Kb-large band, of which the size exactly corresponded to the size of the EcoRI-insert from pLS000. By comparing different DNA amounts, there appeared a copy number of two to five of wun1-wun1 in all tested LS1 plants. In some LS1 plants, there were found additional bands in high molecular regions, probably due to rearranged DNA or undigested DNA.

A functional analysis of the wun1-wun1-DNA of positive LS1 plants was possible on the RNA-level. Both in wounded as well as in non-wounded, untransformed tobacco plants, there was only a weak cross-hybridization with a wun1-cDNA-probe. Additionally, testing was carried out on isolated RNA from untransformed tobacco plants against the 5'-region of the wun1-gene containing the 5'-untranslated region and the wun1-promoter (analogous to the fragment for determining transcription start for the wun1-gene) using S1-analysis on homologous regions. This showed that no wun1-homologous sequences were present, either in non-wounded or in wounded untransformed tobacco leaves or stems.

Out of 30 nopaline-positive LS1 plants studied on the RNA-level, the "Northern Blot" experiment detected 5 plants with high levels of 800 bp-large mRNA hybridizing with wun1. An S1-analysis of the latter led to evidence of two equally large DNA fragments, corresponding in size with fragments from wounded potato leaves. This was the proof to be wun1-homologous mRNA. Several indicators supported the idea that wun1-homologous mRNA is expressed to counteract large-scale TMV attack.

One goal of the invention is the construction and isolation of genes that have the ability to express fused proteins having the desired qualities. For this, it is necessary that the wun1-promoter be solely responsible for the expression of the 3'-fused structure gene, which is not always the case (e.g. proteinase-inhibitor II).

Transcriptional fusions, consisting of the wun1-promoter and 178 bp of the 5'-untranslated gene, were fused with various marker genes (wun1-CAT, wun1-NPT, wun1-GUS), proof thereof being possible through radioactive or fluorimetric methods. (GUS is the name for β-Glucuronidase (Jefferson et al, Proc. Nat. Acad. Sci. 83, 8447-8451 (1987)).

The wun1-CAT construction was tested for transient expression in potato protoplasts. This method made it possible to analyze promoter activity within a few days. For this, highly purified plasmid-DNA containing the construction is transferred into the protoplasten by known methods, remains there in stable condition and can be transcribed and translated. The requirements for expression is that the promoter is functional, and the inducing factors are present in protoplasts handled in this manner.

In these tests, the wun1-promoter, including 179 bp of the 5'-untranslated region, was transcriptionally fused with the Chloramphenicolacetyltransferase-gene (CAT). The construction of the wun1-CAT-fusion is shown in FIG. 10.

The 35S-promoter of the pRT101-CAT plasmid was removed using HincII/XhoI, and instead of this, the 1.0 Kb sized wun1-promoter together with 179 bp of the 5'-untranslated region was inserted using a filled-up EcoRI-site and XhoI. This chimeric gene wun1-CAT was able to be inserted into the PstI-site of the vector pMPK110 (pLS011).

Large amounts of endogenous wun1-mRNA were detected in the potato cell suspension used for transient expression experiments, as well as in the protoplasts derived therefrom. It was concluded that the liquid-cultivation of cells, and in particular the protoplasting step, produces a high stress in the cell, which is indicated by a large yield of wun1-mRNA, analogous to the process in the potato tuber.

For the transient analysis of the wun1-CAT construction, 1 million protoplasts were isolated out of a suspension culture of potato stems of the variety Datura (D12), these being then transformed using the $CaCl_2$/PEG-method by adding 20 micrograms pLS011-DNA.

The CAT-analysis of such protoplasts transformed with pLS011-DNA showed high CAT-activity. A parallel test with a CAMV-35S-CAT-construction (35S-promoter from the cauliflower-mosaic virus (CAMV)) (pRT101-CAT) showed approximately the same CAT activity, whereas in a control test without the addition of DNA, no CAT-activity was detected. This means that, in a transient potato protoplast system, the activity of the wun1-promoter is comparable to that of the 35S-promoter and thus must be classified as very high. Up to the present, the CAMV-promoter stands as the strongest known promoter in plants.

The plasmid pLS011 (wun1-CAT), already used in the transient system, was also used further for the transformation of At $3850_{Km}$. $3850_{Km}$::pLS011 Agrobacteria were used for the transformation of the tobacco species *Samsum NN* (SNN) using the method of leaf disc infection, and the resulting callus were regenerated to plants (LS2).

By the use of this special tobacco species that is resistant to tobacco mosaic virus (TMV), the (suspected) inducibility of wun1 through TMV should be excluded. In LS2-plants, which were nopaline-positive and kanamycin resistant, tests were made on the DNA-level and for the presence of CAT-activity. PstI-digested DNA from wun1-CAT transformed plants exhibited a 2.2 Kb sized fragment hybridized with CAT-cDNA. This exactly corresponded to the expected fragment size of wun1-CAT. No hybridization could be detected in untransformed plants. By comparing DNA-amounts 2 to 4 copies per haploid genome were found in all positive plants.

The functional analysis of LS2-plants continued with the measurement of CAT-activity in greenhouse plants and in plants of the F1-generation grown in sterile culture. LS2-plants raised in the greenhouse showed in their non-wounded leaves a slightly increased CAT-activity, in comparison with the background activity of untransformed tobacco leaves. In wounded leaves an approximately 4-times higher CAT-activity was noted by comparison with non-wounded leaves. However, if an excess of boiled-down potato tuber extract is added to the wounding condition, the increase is 6-times higher than in the non-wounded state. This effect was independent of the condition of the tuber prior to extraction (non-wounded or wounded tubers taken either fresh from the ground or from storage). Each extract had the same inducing effect, pointing to the permanent presence of an inductor in the extract.

The cause of the relatively low inducibility of wun1-CAT in transgenic tobacco plants is to be seen in the activity of non-wounded leaves. In order to eliminate possible causes determined by the greenhouse, the seeds of LS2-plants were harvested, and then germinated under sterile conditions. In young leaves of kanamycin-resistant plants, a very weak CAT-activity was measurable in the non-wounded condition, this being not much different from the CAT-activity of untransformed leaves. In wounded leaves, the CAT-activity rose at least by a factor of 40. The addition of boiled-down extracts from homogenized potato tubers to the wounding condition led to a 60-times higher accumulation of CAT.

Further, it is to be noted that with increasing age of the plants, the activity of the wun1-promoter in the leaves became higher and higher, such that the strength equalled that of a transgenic CAMV-CAT-plant. There is a possibility that the senescence is also capable of inducing wun1.

With the help of the transient system, further tests were made to determine in which plant species the wun1-promoter is active, and correspondingly usable. It turned out that this promoter is not only active in potato protoplasts, tobacco protoplasts and parsley protoplasts, but also showed high expression in rice protoplasts similar to the activity in its homologous system.

Figure 11:
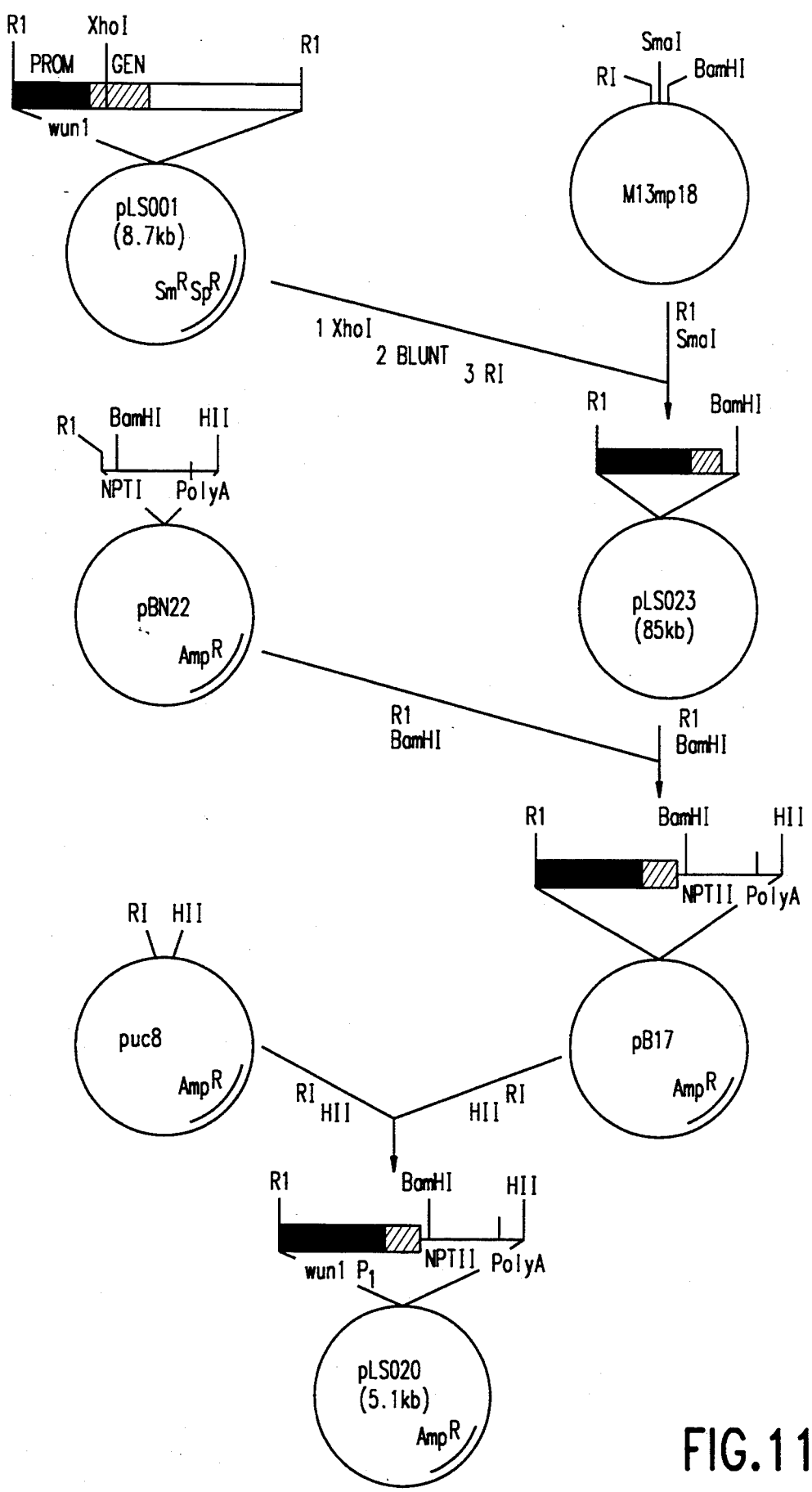
FIG. 11 shows the creation of the wun1-NPTII constructs.

FIG. 11 shows the creation of wun1-NPTII constructs. Beginning from plasmid pLS001, the wun1-promoter is cloned including 179 bp of the 5'-untranslated region at EcoRI-XhoI-blunt of an NPT-II gene (Neomycinphosphotransferase-II). For improved handling in transient experiments, the wun1-NPT-II fusion was recloned in a high copy plasmid (pLS 020).

Using the wun1-NPTII construct, NPT-II activity was found in tobacco and in parsley protoplasts. Interestingly, wun1-dependent NPT-II activity was also detected in rice protoplast (*Oryza sativa japonica* c.v. Taipai), this activity being comparable in its intensity with the wun1-NPTII activity in potato protoplasts. Comparable transient expression of wun1-NPTII and NOS-NPTII (pGV1103) in rice protoplasts likewise showed similarly high values. In this connection, transient expression in potato protoplasts, similar to CAMV-35S-CAT were again indicated. Generally speaking, these studies indicate that the wun1-promoter is capable, at least to some extent, of very high activity, both in homologous and in heterologous systems. Neither in parsley-protoplasts nor in tobacco-protoplasts nor in rice-protoplasts could there be found mRNA hybridized with wun1. Thus one must assume some factor stimulating the wun1-promoter, the factor being equally available in all tested plant species.

Generally speaking, all important DNA-regions are available in the 5'-region of wun1, in order to be able to express a subsequently fused gene in large quantity after wound-induction.

Additionally, the functionality of wun1-CAT and wun1-NPTII in diverse transient systems (potato, parsley, tobacco, rice) as well as in stable transformed tobacco, leads to the assumption of a similar molecular background.

Within the framework of the above invention, investigations further revealed that it can be advantageous to fuse the wun1-promoter of this invention with other promoters or enhancing elements.

An example is the fusing of the wun1-promoter with the known Mannopine-Synthase-(MAS)-Promoter of the *Agrobacterium tumefaciens* TR-DNA.

The isolation of this MAS-Promoter from the *Agrobacterium tumefaciens* TR-DNA is known from the work of J. Velten and J. Schell "Selection-expression Vectors for use in Genetic Transformation of Higher Plants", published in Nucl. Acids Res., 13:6981–6997. From this literature reference, it is also known that this promoter is responsible for the expression of Mannopine-synthase, and shows the following characteristics:

(1) It is bidirectionally active, i.e. if structural genes are fused to both sides, both can be read off in the same regulation manner and intensity. In this connection, reference should be made to the following: Langridge, W. H. R., Fitzgerald, K. J., Koncz, C., Schell, J. and Szalay, A. A. (1989). "Dual promoter of *Agrobacterium Tumefaciens* Mannopine Synthase Genes is regulated by Plant Growth Hormones". Proc. Natl. Acad. Sci. USA, 86:3219–3223.

The orientation of the MAS-promoter has been determined as 1' and 2'.

(2) In transgenic plants, the MAS-promoter can be induced by wounding. A fusion of the MAS2' with the marker gene beta-galactosidase (beta-gal) leads to a higher beta-gal-activity in wounded transgenic tobacco plants than in non-wounded plants.

(3) The activity of the MAS2'-promoter is primarily found in the leaf veins, thus in the vascular system of the leaf. For 2. and 3. reference is made to the following: Teeri, T. H., Lehvaslaiho, H., Franck, M., Uotila, J., Heino, P., Palva, E. T., Van Montagu, M. and Herrera-Estrella, L. (1989). "Gene fusions to lacZ reveal new expression patterns of chimeric genes in transgenic plants". EMBO, 8:343–350.

(4) The characteristics of the MAS1'-promoter have not, up to now, been very intensively researched. However, it is known that the MAS1'-promoter is approximately 4–7 times weaker than the MAS2'-promoter, although aside from this both of the promoters have similar characteristics.

Figure 12:
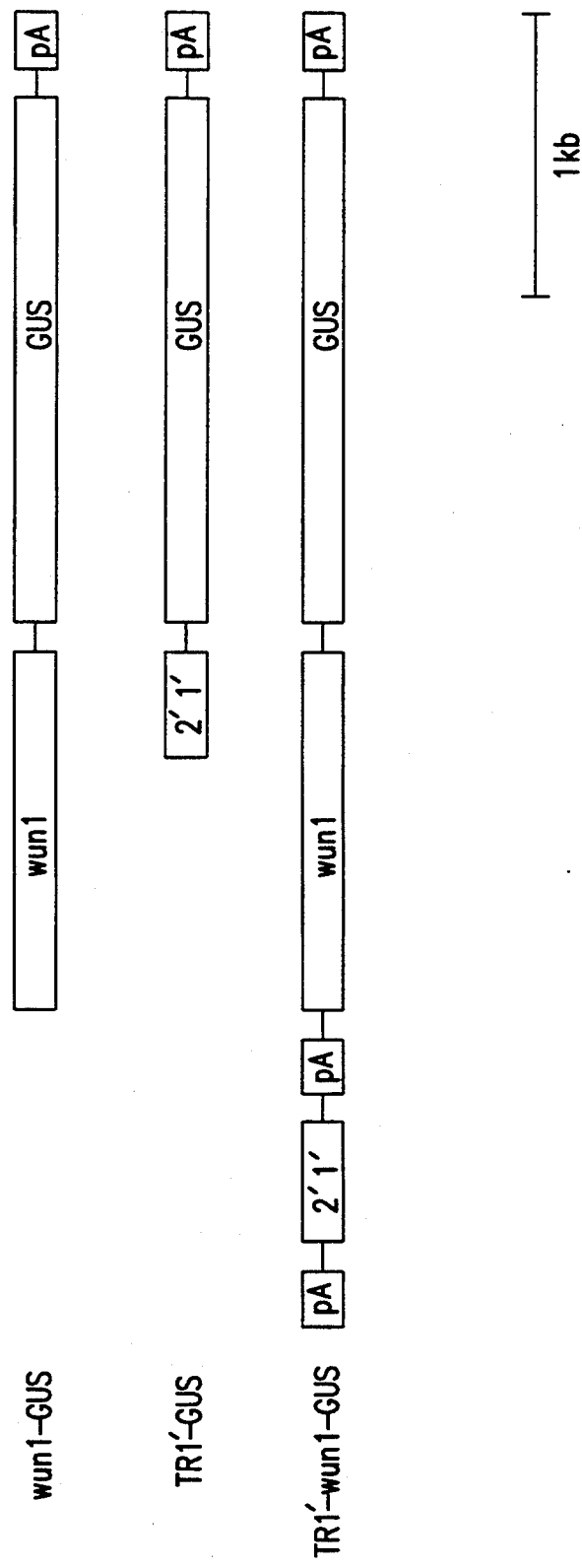
FIG. 12 shows the organization of the clones wun1-GUS, MAS1'-GUS, and MAS1'-wun1-GUS.

Within the framework of researches aimed at a qualitative and quantitative optimization of the wun1-promoter, the MAS-promoter was fused with the wun1-promoter, specifically in the orientation MAS1'-wun1 (FIG. 12).

As evidence of the promoter activity, the marker gene GUS (beta-Glucoronidase) was used (MAS1'-wun1-GUS). Using the *Agrobacterium tumefaciens* transformation system, this construction was transformed into tobacco and analyzed. The following characteristics distinguish this tobacco plant from wun1-GUS transgenic tobacco plants:

1. The tissue specificity had changed. In wun1-GUS transgenic tobacco, the GUS-activity was found primarily in the epidermis of leaves and stems. In MAS1'-wun1-GUS transgenic tobacco, the GUS activity was primarily localized in the vascular system. There is thus the possibility, depending on the scientific requirements, to direct gene products to different locations of the tissue. As against this, the wound-inducibility of MAS1'-wun1-GUS transgenic tobacco plants is comparable with the wound-inducibility of wun1-GUS transgenic tobacco plants.

2. Generally, the activity of the MAS1'-wun1-promoter in transgenic tobacco leaves and tobacco stems is approximately 10 times higher than the activity of the unw1-promoter. Hence, the MAS1'-wun1-promoter appears to be among the strongest promoters available for gene expression in plants.

3. While promoter activity in transgenic dicotyl plants currently presents little problem, there have been few promoters up to now which are fully active in monocotyl plants (to which the commercially important grain plants belong). Transient development studies in rice protoplasts (these serve as substitute for studies in transgenic rice-plants, which are very difficult to obtain) show that the MAS1'-wun1-promoter has roughly 30 times higher activity than the wun1-promoter. This is all the more remarkable because even the 35S-promoter which is so strong in dicotyl plants is here 30 times weaker than the MAS1'-wun1-promoter.

Thus, the wun1-promoter, according to the invention, can, for example, be altered or optimized in the following characteristics, through fusion with the MAS1'-promoter:

(a) The specific activity of the wun1-promoter in the leaf or stem epidermis of transgenic tobacco can be targeted to the vascular system through fusion with the MAS1'-promoter;

(b) The capacity of the wun1-promoter for being induced through wounding is not changed through fusion;

(c) The MAS1'-wun1-promoter is approximately 10 times stronger than the wun1-promoter alone, in transgenic tobacco leaves and stems;

(d) In transient experiments with a substitute for monocotyl plants (rice), the MAS1'-wun1-promoter is roughly 30 times stronger than the wun1-promoter.

In accordance with the invention, for example, the expression of the wun1-promoter through fusion of the same with an enhancing element of the CamV-35S-promoter can be increased. Thus, for example, the fusion of the enhancing element of CamV-35S-promoter at the 5'-end of the wun1-promoter leads to an increased activity of the wun1-promoter in transgenic tobacco and potatoes.

FIG. 12 shows the organization of the clones wun1-GUS, MAS1'-GUS and MAS1'-wun1-GUS.

Figure 13:
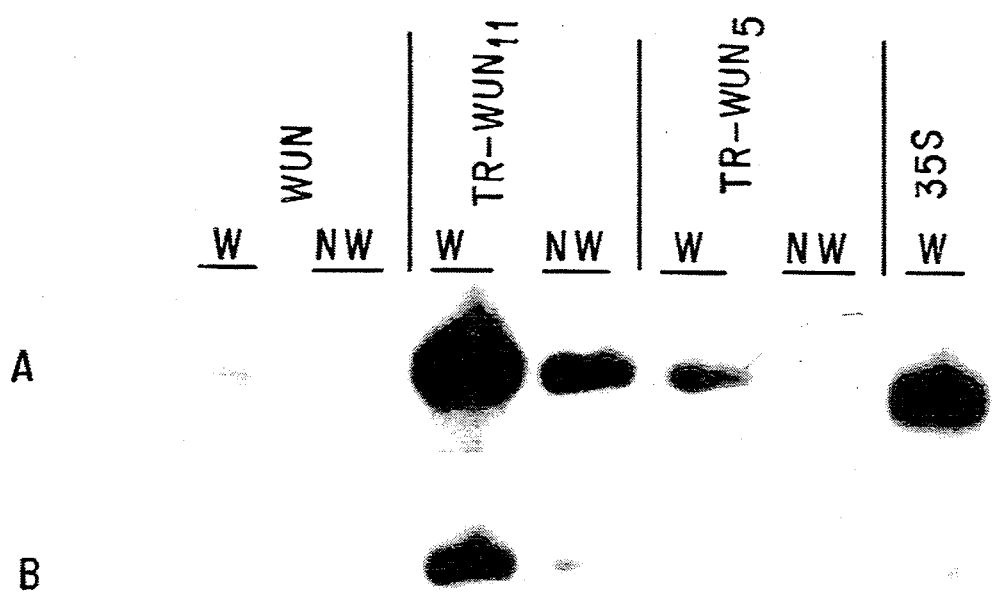
FIG. 13 shows the result of "Northern blot" analysis of wounded and non-wounded transgenic tobacco leaves.

FIG. 13 shows the Norther-Blot-analysis of wounded and non-wounded transgenic tobacco leaves. Non-wounded (NW) and wounded (W) leaves of the transgenic tobacco plants wun1-GUS, MAS1'-wun1-GUS Nr.5 and Nr.11 and 35S-GUS were used for the isolation of RNA. In each case, 50 micrograms of the total RNA was separated gel-electrophoretically using a 1.2% formaldehyde gel, then transferred to a nylon membrane, then hybridized with a radioactively labelled GUS-DNA probe, and visualized on an autoradiogram. (A) shows a 2-day old exposure, (B) shows a 6-hour old exposure.

The examples below serve to clarify the invention:

EXAMPLES 1–8

Materials

Media

Culture media for bacteria:

The media used for the growth of bacteria were established on the basis of data from Maniatis et al., "Molecular Cloning: A Laboratory Manual", Cold Spring Harbour Laboratory, Cold Spring, Harbour, N.Y. (1982):

Plant Media:

The media utilized were derived from the media given by Murashige and Skoog, Physiol. Plan. 15 473–497 (1962), (MS).

MS: MS+3% Sucrose

MSC: MS+3% Sucrose, 500 micrograms/ml Claforan

MSC10: MS+2% Sucrose. 500 micrograms/ml Clarofan, 0.2 micrograms/ml NAA, 1 microgram/ml BAP 100 micrograms/ml Kanamycinsulphate MSC15: MS+2% Sucrose, 500 micrograms/ml Claforan, 100 micrograms/ml Kanamycinsulphate MS15: MS+2% Sucrose, 100 micrograms/ml Kanamycin-sulphate For solid media, 8 g/l of Bacto-Agar was added.

Strains and Vectors

E. coli-strain:
BMH 71-18: (lac-proAB), thi, supE; F'(laci$^q$. ZdeltaM15, proA+B+) (Messing et al., Proc. Nat. Acad. Sci. 74, 3642-2646 (1977))
C 600: =CR34 (Maniatis et al. 1982)
GJ23: AB1157 (R64drd11) (pGJ28) (Van Haute et al., EMBO J. 2, 411-418, (1983))
Agrobacteria-strains: C58ClpGV3850$_{KM}$ (Zambryski et al., EMBO J. 1, 147-152, (1983))
Plasmids: pUC8 (Vieira and Messing, Genes 19, 259-268 (1982)) pMPK110 (Eckes et al., Mol. Gen. Genet. 205, 14-22 (1986)); pRT101-cat (Pröls et al., Plant Cell Reports, in print (1988)); pGV1103 (Hain et al., Mol. Gen. Genet. 199, 166-168 (1985))
Phages: EMBL4 (Frischauf et al., J.Mol. Biol. 170, 827-842 (1983)); M13mp18 (Yanisch-Perron et al., Gene 33, 103-119, (1985)); M13mp19 (Yanisch-Perron et al., (1985))

Plants:
Solanum tuberosum AM 80/5793 (haploid), Berolina (tetraploid), Datura (D12), Granola
Nicotinia tabacum Wisconsin 38 (W38), Samsum NN (SNN)
Oryza sativa japonica c.v. Taipai All molecular biological standard methods, such as restriction analysis, plasmid isolation, mini-preparation of plasmid-DNA, transformation of bacteria and so on, were carried out as described by Maniatis et al., (1982) unless otherwise indicated.

Wounded Plant Tissue

Potato tuber material was cut into slices 3 mm thick, and incubated in a phosphate solution (20 mM phosphate buffer, pH 7.0, with chloramphenicol (50 micrograms/ml)) for 18 hours at 28° C. in the absence of light. Leaf material, stem material and root material was cut into small pieces and incubated under the same conditions. After the completion of incubation, the material was either directly processed or stored at −70° C.

Non-Wounded Plant Tissue

Leaf material, stem material, root material and tuber material was processed immediately after removal from the living plant, or frozen in liquid nitrogen and stored at −70° C.

Aerobic Wounding of Potato Tubers

Treatment as described under "wounding", in which during the incubation the tuber slices were only lightly wetted with the phosphate buffer. After the incubation, the potato surfaces were brown.

Anaerobic Wounding of Potato Tubers

Treatment as described under "wounding", in which during the incubation the potato slices were fully submerged in the phosphate buffer. After the incubation, the tuber surfaces were bright yellow-white.

Development of wun1-mRNA in Pathogen-Attacked Potato Leaves

Leaves of the species "Datura" were cut away at the leaf stem and placed in water along with the stem. Then the leaves were sprayed with a suspension containing phytophtora-spores. At different times, the complete RNA of a given leaf could be isolated and investigated using the "Northern-Slotblot-Analysis". Three different materials were used:
Water, containing the spores of a Datura-compatible phytophtora infestans species Pi1;
Water, with the spores of a Datura-incompatible phytophtora infestans species Pi4;
Water, without addition of spores (control)

Two hours after the treatment of the leaves with water and spores of the incompatible phytophtora species, densitometric evaluation of the strength of the wun1-hybridization indicated a 4-times increase in the amount of wun1-mRNA. From the fourth to the eighth hour, the amount remained approximately the same, whereupon it fell gradually up to the 30th hour back to the 1.5 to 2-times value. The same development ratios were found for wun1-mRNA when using water without spores (control).

In the analogous trial using water and compatible phytophtora spores, a 4-times increase in wun1-mRNA was seen 2 hours after the attack, this factor only slightly reducing up to the 10th hour. From the 16th hour at the latest, the factor increased to about 6-times the control value, and then constantly rose to reach a factor of 9 after 30 hours.

Wounding with the Addition of Potato Extract

Potato tubers were homogenized at 4° C. without the addition of buffers, and then centrifuged for 10 minutes at 10,000 rpm in an SS34-rotor.

The remaining material was cooked for 10 minutes and then again centrifuged. The clear supernatant was added in the ratio of 1:10 to 20 mM phosphate buffer, pH 7.0, and the tissues to be tested were then incubated under the usual conditions.

EXAMPLE 1

RNA-Isolation

The isolation of RNA from various organs of the potato and the tobacco plant were carried out as described by Logemann et al. in Anal. Biochem., 163:16-20 (1987).

The selective concentration of PolyA+RNA was done using mAP-papers (Werner et al., Analytical Biochem. 141, 329=336 (1984)).

"Northern-Blot" Analysis

The RNA was separated electrophoretically on a 1.5% formaldehyde-agarose-gel (Lehrach et al., Biochemistry 16, 4743, (1977)). As described by Willmitzer et al., EMBO J. 1. 139-146, (1982), the RNA was next transferred to nitrocellulose, fixed and hybridized with $^{32}$P*radioactively marked cDNA, grown and exposed.

DNA-Isolation

Nuclear DNA was obtained according to the method of Bedbrook, PMB Newsletter II, 24 (1981) from potato leaves and used for the cloning procedure in Lambda Phages EMBL4. DNA from the transformed tissues was isolated and purified using Triton X-100, SDS, and proteinase K (Wassenegger, Dissertation, Köln (1988)).

"Southern-Blot"-Analysis

DNA was electrophoretically separated on 0.8 to 1.2% Agarose gel, transferred to nitrocellulose and fixed (Southern, J. Mol. Biol. 98, 503-517 (1975)), and hybridized and washed as described by Willmitzer et al (1982).

"Run-Off" Experiments

A method which relatively accurately distinguishes between the two regulation types (transcriptional and translational regulation) is the "run-off" method. In this method, cell nuclei from wounded and non-wounded tubers are isolated, and newly synthesized mRNA therefrom is radioactively pulse-labelled and hybridized with single strand DNA of the individual clones. In cell nuclei from non-wounded clones, no wun1-mRNA was produced. By contrast, in cell nuclei from wounded tubers, this material was produced in high quantity.

The isolation of cell nuclei from potato tubers, as well as the subsequent in-vitro transcription, were carried out in accordance with Willmitzer et al., Nucl. Acids Res. 9, 19 (1981). The radioactively labelled RNA-transcripts obtained by this method were hybridized with bidirectional M13 cDNA-clones.

Protein Isolation and Splitting

The isolation of proteins from potato tubers as well as the 1-dimensional and 2-dimensional gel-electrophoretical separation thereof, has been described by Mayer et al., Plant Cell Reports 6, 77–81, (1987).

EXAMPLE 2

"Hybrid-Released-Translation"-Experiments

The 800 bp fragment of the cDNA-clone wun1-25A2 and the 700 bp fragment of the cDNA-clone wun2-29C12 were cloned in M13mp18 using the PstI sites. The orientation of the insertions in the M13-clones were determined by complementation analyses (Messing, in: Genetic Engineering of Plants, (1983), Plenum Press, New York, 1983). The identification of the M13-clone containing the coding strand resulted from positive hybridization with radioactively labelled polyA+RNA from wounded potato tubers.

The isolation of single strand DNA from M13 phages (they contain the coding strand), the fixation of this DNA on nitrocellulose and the hybridization with potato tuber RNA, as well as the wash and release of selected RNA, has been described by Maniatis et al (1982). The selected RNA as well as the polyA+RNA isolated from the potato tubers were translated in a rabbit-reticulocyte-lysate (Pelham and Jackson, Eur. J,. Biochem. 67, 247 (1976)) in the presence of 35S-Methionin. The 1-dimensional and 2-dimensional electrophoretic separation on a polyacrylamide-gel was carried out according to Mayer et al (1987).

EXAMPLE 3

Establishment and Screening of a Genomic Bank

Isolation of genomic DNA:

According to the methods of Bedbrook (1981), isolated leaf DNA of the haploid line AM 80/5793 was used as genomic potato DNA.

This DNA was fully digested with EcoRI.

Isolation of the phage-DNA:

EMBL4-DNA was cut into three fragments with EcoRI, wherein after gel-electrophoretic separation and subsequent fragment isolation, the two vector arms of the middle fragment could be separated. In addition, commercially available purified EMBL4-arms were also used (Amersham).

Ligation and Loading:

After subsequent ligation of the EMBL4-arms with the EcoRI-digested genomic DNA, the ligated, high-molecular DNA was loaded in vitro into phage heads.

(Hohn and Murray, Proc. Nat. Acad. Sci. USA, 74, 3259–63, (1977); Hohn, Meth. Enzym. 68, 299–309 (1979)). The loading material derived from a "Lambda in vitro packaging kit" of the company Amersham. The genomic bank was plated out with a concentration of 25.000 plaques per plate (25×25 cm).

Plaque hybridization:

The detection of cDNA-homologous Lambda-clones resulted from a plaque hybridization according to Benton and Davies, Science 196, 180 (1977) using a radioactively labelled cDNA. Positively hybridising plaques were isolated and again tested.

DNA-Preparation of Recombinant Phages:

20 ml of a C600-lysed bacterial culture was mixed with chloroform in order to obtain, after subsequent centrifugation, a bacteria-free supernatant. The sedimentation of the phages from the supernatant was carried out by a 4-hour centrifugation at 10,000 rpm. The phage sediment was removed in 500 microliters phage-buffer (10 mM Tris-HCl, pH 8.0, 10 mM $MgCl_2$) and treated with DNase and RNase. After the extraction of the DNA through repeated phenolysation, the phage DNA was EtOH-precipitated, washed with 70% EtOH and removed in TE.

EXAMPLE 4

Creation of Deletion Mutants after Exonuclease-III-Treatment

The fragment to be investigated was cloned in both orientations in M13mp19, in accordance with Henikoff et al., Gene 28, 351–359 (1984). Since the exonuclease III digests 5' overhanging ends, while the 3' overhanging ends remain, 20 microgram of the DNA to be analyzed was digested by two restriction enzymes, creating 5'-end and a 3'-end. Because the 5'-end was located towards the fragment, an exonuclease-digestion of the fragment could take place. Using repeated stopping of this reaction, it was possible to isolate 200 bp smaller fragments, of which the sticky ends were changed into ligatable blunt ends through a subsequent S1 treatment. Finally, there followed the transformation of this DNA in BMH 7118-cells, and then the single strand DNA isolation.

Sequencing

The sequencing of single strand DNA was carried out according to the chain interruption method of Sanger et al., Proc. Natl. Acad. Sci. USA 74, 5463, (1977). The separation of the reaction materials was done on 6% and 8% sequence gel (Ansorge amd de Mayer, J. Chromatogr. 202, 45–53 (1980); Ansorge and Barker, J. Biochem. Biophys. Meth. 9, 33 (1984)).

Cloning and Sequencing of wun1-25A2

The approximately 711 bp-sized insert of the clone wun1-25A2 was cloned with its PstI-site in the M13mp19-vector. The orientation of the insert was analysed using the asymmetric XhoI-site. The clones 25A2-4-mp19 and 25A-5-mp19, differing in the orientation of the insert, were digested with KpnI/XbaI, in order to make possible a bidirectional exonuclease III digestion of the fragment. Deletion clones of different sizes could be obtained by successive stopping of the exonuclease reaction. These deletion clones served as purified single strand DNA for sequencing in accordance with the method of Sanger et al (1977).

EXAMPLE 5

S1-Analysis

The principle of S1-nuclease mapping for the determination of transcription starting sites is based on the concept that, through a hybridization of single strand DNA from the 5'-region of the wun1-gene with wun1-mRNA, only those regions are protected against destruction by the single strand-specific nuclease S1, which on the basis of its homology, can form a double strand. The size of the protected DNA fragment can be determined on a sequencing gel, and thus the transcription start can be traced back.

The determination of the transcription start point was carried out according to Berk and Sharp, Proc. Natl. Acad. Sci. USA 75, 1274 (1987). For this, the 1.2 kb fragment was isolated from the plasmid pLS000 with EcoRI and XhoI, and dephosphorylated with phosphatase. Finally, there followed a radioactive labeling of the 5'OH-ends through the combination of polynucleotidekinase and y-$^{32}$P-ATP. After denaturing the DNA-fragments, they were hybridized with 50 micrograms of whole RNA (hybridization buffer: 80% formamide, 0.4 mM NaCl, 40 mM PIPES pH 6.4 and 1 mM EDTA). This condition favours RNA-DNA-hybrids in comparison to DNA-DNA hybrids (Casey and Davidson, Nucl. Acids Res. 4, 1539–1552 (1977)). The hybridization temperature started near 80° C. and was lowered overnight to 40° C. A subsequent S1-nuclease digestion (120 U/ml) removed unpaired strands. It was expected that the radioactively labelled XhoI site located at the 5'-untranslated region of the wun1-gene would be protected due to its homology to mRNA. Finally, the S1-protected DNA strand was electrophoretically separated on a sequencing gel, so that the sequence of a known DNA-fragment would serve as a size marker.

EXAMPLE 6

Transient Expression in Potato Protoplasts

Quantities of 20 micrograms of highly purified (CsCl-gradient) plasmid-DNA was transformed in potato protoplasts treated with PEG/CaCl$_2$ (Lipphardt, Dissertation, Köln, 1988). The protoplasts were isolated from a potato stem suspension culture of the species *Datura*.

Transient Expression in Rice Protoplasts 20 micrograms of highly purified (CsCl-gradient) plasmid DNA was transformed in accordance with the modified method by Lörz et al., Mol. Gen., Genet. 199, 178–182 (1985). The concentration of polyethylene glycol and osmoticum were altered.

EXAMPLE 7

DNA-Transfer in Agrobacteria

Conjugation:

DNA cloned in *E. coli* was transferred using the helper strains GJ23 into the Agrobacteria species 3850$_{km}$, according to the method described by Van Haute et al. (1983).

DNA-analysis of Agrobacteria:

The monitoring of the DNA transfer into the Agrobacterium was carried out through the isolation of Agrobacteria DNA according to the method described by Murray and Thompson, Nuc. Acid Res. 8, 4321–4325 (1980). Restriction digestion of the DNA, the transfer to nitrocellulose and the hybridization with the corresponding radioactive probe, point out a successful DNA-transfer into the Agrobacteria.

EXAMPLE 8

Transformation of Tobacco

Growth of Agrobacteria:

The Agrobacteria 3850$_{Km}$ necessary for infection, were grown in selective antibiotic media (Zambryski et al., 1983), sedimented through centrifugation and washed in a YEB-medium without antibiotics. After another sedimentation and resuspension in YEB-medium, the bacteria can be used for infection.

Leaf Disc-Infection:

Sterile leaves of the tobacco lines SNN and W38 were used for the leaf disc-infection. Leaf pieces about 1 cm in size were sterilized by a 10-minuted incubation in 0.1% HgCl$_2$, 0.1% SDS, and then washed three times in sterile water. There followed the submersion in an Agrobacterium suspension as described above, and the subsequent transfer to 3MS-medium. After a two-day incubation with 16 hours under light and at about 25° C. to 27° C., the leaf pieces were washed several times in liquid 3MS-medium, and transferred to 3MSC-medium. After 4–6 weeks, shoots which emerged were isolated and incubated on a 2MSC-medium. As further evidence of a successful transformation, the nopaline test was carried out.

Analysis of the Transformed Plants

Evidence of nopaline-synthase activity:

The detection of nopaline-synthase activity in transformed plant leaves was carried out according to Otten and Schilperoort, Biochem. Biophys. Acta 527, 497 (1978).

Proof of NPT-II-Activity:

The NPT-II-activity in transformed plants was established in accordance with Reiss et al., Gene 30, 217–223 (1984) and Schreier et al., EMBO J., 4, 25–32 (1985).

Proof of CAT-Activity:

Chloramphenicol-acetyl-transferase (CAT) activity was determined according to the method of Velten and Schell, Nuc. Acids, Res. 13, 6981–6997 (1985) and Herrera-Estrella et al., EMBO J. 2, 987 (1983).

EXAMPLE 9

Optimization of the wun1-Promoter by Fusion with the TR-Promoter (TR1'wun1)

For the media used, reference may be had to Examples 1–8.

2.1.4. Species and Vectors

Agrobacterial species: GV3101pmp90RK (Koncz, C. and Schell, J. "The promoter of TL-DNA gene 5 controls the tissue-specific expression of chimeric genes carried by a novel type of Agrobacterium binary vector", (1986), Mol. Gen. Gent. 204:383–396).

Plasmids:
pPCV720 (thus far unpublished Plasmid by Dr. Koncz, MPI f. Züchtungsforschung, Köln)
35S-GUS=pRT99-GUS (Töpfer, R., Schell, J. and Steinbiβ, H. H. "Versatile cloning vectors for transient gene expression and direct gene transfer in plant cells." (1988)
wun1-GUS (Siebertz, B., Logemann, J., Willmitzer, L., Schell, J. "Cis-analysis of the wound-inducible promoter wun1 in transgenic tobacco plants and histochemical localisation of its expression". The Plant Cell, in print (1989)

MAS1' (TR1')-wun1-GUS (Logemann et al., in print)

MAS1' (TR1')-GUS (Logemann et al, in print)

Plants:

*Nicotiana tabacum* Wisconsin 38 (W38)

METHODS

All molecular biological standard methods, such as, for example, Restriction Analysis, Plasmid Isolation, Mini-preparation of Plasmid-DNA, Transformation of Bacteria and so on, were carried out as described by Maniatis et al, (1982), unless otherwise indicated.

Wounded and non-wounded Plant Tissue was obtained as described in Examples 1–8.

Reference to Examples 1–8 can also be had in connection with the RNA-isolation, the "Northern Blot" analysis, the DNA-isolation, the transient expression in rice protoplasts, the "Southern Blot" analysis an the DNA-analysis of Agrobacteria.

DNA-Transfer into Agrobacteria

The DNA cloned in *E. coli* was transferred into the Agrobacteria species GV3101pmp90RK, in accordance with the method described by Van Houte, E., Joos, H., Maes, M., Warren, G., Van Montagu, M., Schell, J. "Intergenic transfer and exchange recombination of restriction fragments cloned in pBR322: a novel strategy for reversed genetics of Ti-plasmids of *Agrobacterium tumefaciens*", EMBO J., 2:411–418.

Transformation of Tobacco

Culture of Agrobacteria

The Agrobacteria GV3101pmp90RK, containing the desired plasmid, were grown in a selective antibiotic medium (Hygromycin), sedimented by centrifugation and washed in YEB-medium (Maniatis et al, 1982) without antibiotics. After further sedimentation and removal in YEB-medium, the bacteria could be used for infection.

Leaf Disc-Infection

This was carried out as described in Example 8, however without the use of the nopaline test.

Analysis of the Transformed Plants

Proof of GUS-activity

A: The fluorometric analysis of beta-glucoronidase-activity (GUS-activity) was carried out in accordance with the methods of Jefferson, A. R., Kavanagh, T. A., Bevan, M. W. "Gus-Fusions: β-Glucoronidase as a sensitive and versatile gene fusion marker in higher plants", EMBO J. 6:3901–3907 (1987).

B: Blue—staining of tissue in relation to GUS-activity could be obtained using X-Gluc solution. X-Gluc solution. 1-2 mM X-Gluc (5-Bromo-4-chloro-3-indolyl-glucuronide), and dimethyl formamide were dissolved in 50 mM phosphate-buffer at pH 7.0.

Wounded Tissues:

Thin tissue slices were incubated as described under "Wounded Plant Tissues" and then stained overnight at 37° C. in X-Gluc solution. Finally, the chlorophyll was removed by the addition of 100% methanol at 60° C.

Non-wounded Tissues:

Thin tissue slices were incubate in X-Gluc solution which additionally contained the translational inhibitor Cycloheximide (1.8 mM). The incubation period and the methanol treatment are the same as with the wounded tissue.

X-Gluc staining of Pollen:

Pollen was incubated overnight at 28° C. in 30% sucrose, leading to the development of pollen tubes. Finally, a doubly concentrated 30% X-Gluc solution was added and the pollen were incubated overnight at 28° C. Alternatively, the pollen grains are incubated directly in X-Gluc, without developing pollen tubes.

RESULTS

Organization of MAS1'-wun1-Gus, MAS1'-GUS and wun1-GUS (FIG. 12)

wun1-GUS:

1022 bp of the wun1-promoter and 178 bp of the wun1 5'-untranslated region were transcriptionally fused with the beta-Glucuronidase-Gene (GUS). The polyadenylation signal (pA) of the nopaline-synthase-gene was used (NOS) as a termination sequence.

MAS1'-GUS:

The MAS1'-promoter was fused transcriptionally with the GUS-gene, and terminated by the pA-signal of the NOS-gene.

MAS1'-wun1-GUS:

Behind the 1'-promoter of the MAS-promoter the pA-signal of the octopine-synthase-gene (OCS) was cloned in order to suppress a transcription through the wun1-promoter. Behind the OCS pA-signal the wun1-promoter (1022 pb) is located, including (in homology to the wun1-GUS construction) 179 bp of the untranslated 5' region of the wun1-gene which are transcriptionally fused with the GUS-gene. The pA-signal of the 35-S gene serves as the termination sequence for the GUS-gene. This construction (MAS1'-wun1-GUS) is present in the binary vector pPCV720, which can replicate in both *E. coli* and in Agrobacteria (with the help of a helper plasmid).

RNA-Analysis of MAS1'-wun1-GUS Transgenic Tobacco

RNA from wounded and non-wounded leaves of various MAS1'-wun1-GUS transgenic tobacco plants, as well as from wun1-GUS and 35S-GUS transgenic tobacco leaves, was isolated and hybridized with radioactively labelled GUS-DNA.

As is shown in the Northern-Blot in FIG. 13, 1. the GUS-mRNA in transgenic MAS1'-wun1-GUS-leaves is exactly as large as in wun1-GUS transgenic leaves. It appears that in both constructions, the same transcription start was used.
2. the amount of RNA in wounded leaves, both in MAS1'-wun1-GUS-plants and in wun1-GUS-plants, is higher than in non-wounded leaves. The wound-inducibility already known for wun1-GUS was also true for MAS1'-wun1-GUS.
3. from an RNA quantity comparison, it was realized that somewhat more RNA was to be found in wounded MAS1'-wun1-transgenic leaves than in 35S-GUS transgenic leaves. Since the 35S-promoter is one of the strongest promoters in plants, the MAS1'-wun1-promoter is estimated of similar strength.

Analysis of GUS-activity in Transgenic Tobacco

A quantitative analysis of GUS-activity of transgenic TR1'-wun1-GUS plants shows that the MAS1'-wun1-promoter in transgenic leaves is inducible by wounding at a factor of 2 times up to 13 times (on average about six times). This observation is similar to the wound inducibility of the wun1-promoter in transgenic leaves (Logemann J., Lipphardt S., Lörz, H., Häuser, I., Willmitzer, L. and Schell J. "5'upstream sequences from the wun1-gene are responsible for gene activation by wounding in transgenic plants" The Plant Cell 1:151–158 (1989A)). Analogously to the transgenic wun1-GUS tobacco plants, the wound inducibility in the higher, younger leaves is the highest, while, in the lower, older leaves it is the smallest. The reason for this difference in inducibility is the increasing activity, from top to bottom, of the MAS1'1-wun1-promoter in non-wounded tissue. In old leaves of old plants, the activity of the MAS1'-wun1-promoter in non-wounded condition is already so high that wounding cannot induce any further activity (analogous to wun1-GUS plants).

A relative comparison of promoter-activities in transgenic tobacco leaves and stems shows that the wun1-promoter is roughly 10 times stronger than the MAS1'-promoter. The MAS1'-wun1GUS promoter, on the other hand, is 10 times stronger than the wun1-promoter. Consequently, the MAS1'-wun1-promoter is roughly 100 times stronger than the MAS1'-promoter.

Localization of GUS-Activity in Transgenic Tobacco

Leaf, Stem:

The GUS-activity in the tissue slices from wounded and non-wounded leaves and stems of wun1-GUS and MAS1'-wun1-GUS transgenic tobacco was localized by the use of the substrate X-Gluc.

wun1-GUS:

As can be seen from the blue colored regions, the activity of the wun1-promoter is limited primarily to the epidermis (including trichome), and to a lesser extent the vascular system of wounded leaves (W). In non-wounded leaves (NW), on the other hand, only a small wun1-promoter-activity can be seen in the epidermis, and no activity in the vascular system. The same results were obtained also with stem cross-sections.

Accordingly, the wun1-promoter activity is to be regarded as epidermis-specific in leaves and stems.

In MAS1'wun1-GUS plants, an intensive blue coloring in the vascular system of wounded plant slices is recognized. In other regions (epidermis, parenchyme), the coloring is weak. Non-wounded leaf slices show a low level of blue coloring in the vascular system, and no color in the epidermis. The same results were found with stem cross sections.

This appears to suggest, in connection with MAS1-'wun1-GUS, a vascular-specific expressing promoter in leaves and stems.

Leaf cross-sections of MAS1'GUS plants were used as control. Because of the weak promoter activity of the MAS1'-promoter (10 times weaker than the wun1-promoter), blue staining was not found in either wounded or non-wounded leaf cross sections.

Anthers:

An X-Gluc staining of anther cross-sections as well as of pollen shows the following characteristics, which apply both for wun1-GUS and for MAS1'-wun1-GUS:

A blue staining (and GUS-activity) was detected in the stomium (the natural perforation location of the anther in order to release pollen) and in the pollen. In separated ungerminated pollen and germinated pollen, there was found a blue staining in the pollen grain and in the pollen tube.

Transient Expression with Rice-Protoplasts

The constructions MAS1'-wun1-GUS, wun1-GUS, MAS1'-GUS and 35S-GUS were used for studies of transient development with rice protoplasts of the variety Oryza sativa japonica c.v. Taipai. As shown in Table 1, the activity of MAS1'-GUS is not significantly different from the control (GUS-activity of rice-protoplasts), which were transformed without DNA). wun1-GUS and 35S-GUS show a 2 times to 3 times higher activity than the control. By contrast, MAS1'-wun1-GUS DNA exhibits on average a 57-times higher activity than the control, and therefore is a highly active promoter in rice protoplasts.

TABLE 1

| Construction | GUS-Activity nmol MU/mg/min | Relative GUS-Activity |
|---|---|---|
| MAS-GUS | 31 | 1.2 |
| wun-GUS | 59 | 2.3 |
| MAS-wun-GUS | 1416 | 56.7 |
| 35S-GUS | 66 | 2.6 |
| Control | 25 | 1.0 |

Legend for Table 1: The given GUS-activity was based on 5 independent tests.

The results of Table 1 are seen through the staining of the protoplasts with X-Gluc. Only protoplasts transformed with MAS1'-wun1-GUS show an intensive blue staining.

We claim:

1. A purified and isolated DNA molecule having a nucleotide sequence shown as residues 1–2368 in FIG. 6 (SEQ ID NO: 5).

2. A purified and isolated DNA molecule comprising residues 1–1022 of the sequence set forth in FIG. 6 (SEQ ID NO:5).

3. A purified and isolated DNA molecule comprising the structural gene portion of the DNA molecule of claim 1 as contained in residues 1238–1552 of the sequence set forth in FIG. 6 (SEQ. ID NO:5).

4. A DNA-transfer vector with an inserted DNA molecule according to claims 1, 2 or 3.

5. A DNA-transfer vector which comprises a wound-inducible promoter having a sequence as set forth for residues 1–1022 in FIG. 6 (SEQ. ID NO:5) operably linked to a structural gene which is not the structural gene encoded by residues 1238–1552 of FIG. 6 (SEQ ID NO:5).

6. A plant or plant material containing a DNA molecule according to claim 5, wherein the plant or plant material is a tobacco plant or a tobacco plant material.

7. A plant or plant material containing a DNA molecule according to claim 5, wherein the plant or plant material is a potato plant or potato plant material.

* * * * *

UNITED STATES PATENT AND TRADEMARK OFFICE
CERTIFICATE OF CORRECTION

PATENT NO. : 5,428,146          Page 1 of 2

DATED : June 27, 1995

INVENTOR(S) : Logemann et al.

It is certified that error appears in the above-indentified patent and that said Letters Patent is hereby corrected as shown below:

On the title page, Item 56, 8th line, "Sanchez-Serano" should read --Sanchez-Serrano--;

On the title page, Item 56, 4th-from-bottom line, "Harbor" should read --Harbour--;

Col. 1, lines 37-38, "concentration" should read --concentrations--;

Col. 2, line 65, "expresion" should read --expression--;

Col. 3, line 36, "wun1-mRNA" (second occurrence) should read --wun2-mRNA--;

Col. 5, line 21, "rougly" should read --roughly--;

Col. 6, line 3, "sizing" should read --sizing of--;

Col. 11, line 56, "unw1-promoter" should read --wun1-promoter--;

Col. 12, line 30, "Norther-Blot-analysis" should read --Northern-Blot-analysis--;

Col. 12, line 58, "MS" (first occurrence), should read --3MS--;

Col. 12, line 59, "MSC" should read --3MSC--;

UNITED STATES PATENT AND TRADEMARK OFFICE
CERTIFICATE OF CORRECTION

PATENT NO. : 5,428,146

DATED : June 27, 1995

INVENTOR(S) : Logemann et al.

It is certified that error appears in the above-indentified patent and that said Letters Patent is hereby corrected as shown below:

Col. 13, line 7, "3642-2646" should read --3642-3646--;

Col. 15, line 46, "35S" should read --$^{35}$S--;

Col. 16, line 55, "Sequencing" should read --Sequencing--;

Col. 18, line 17, "10-minuted" should read --10-minute--;

Col. 19, line 19, "an" should read --and--;

Col. 22, line 29, "DNA)" should read --DNA--.

Signed and Sealed this

Twenty-seventh Day of August, 1996

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,428,146
DATED : June 27, 1995
INVENTOR(S) : Logemann et al.

It is certified that error appears in the above-indentified patent and that said Letters Patent is hereby corrected as shown below:

On the title page, item [73], add "der Wissenschaften E.V." to the Assignee's name.

Signed and Sealed this

Twenty-ninth Day of October 1996

Attest:

BRUCE LEHMAN

*Attesting Officer*     *Commissioner of Patents and Trademarks*